(12) United States Patent
Yeung et al.

(10) Patent No.: US 11,130,228 B2
(45) Date of Patent: Sep. 28, 2021

(54) ROBOTIC ARM SYSTEM WITH GEAR-DRIVEN END-EFFECTOR ASSEMBLY

(71) Applicant: Bio-Medical Engineering (HK) Limited, Hong Kong (CN)

(72) Inventors: Chung Kwong Yeung, Hong Kong (CN); Jianwei Zhang, Hong Kong (CN); Tsun Ping Jimmy To, Hong Kong (CN); Wai Lik Alik Chan, Hong Kong (CN)

(73) Assignee: Bio-Medical Engineering (HK) Limited, Hong Kong (CN)

( * ) Notice: Subject to any disclaimer, the term of this patent is extended or adjusted under 35 U.S.C. 154(b) by 0 days.

(21) Appl. No.: 16/860,593

(22) Filed: Apr. 28, 2020

(65) Prior Publication Data
US 2020/0254608 A1    Aug. 13, 2020

Related U.S. Application Data

(63) Continuation of application No. 16/290,402, filed on Mar. 1, 2019, now Pat. No. 10,632,613, which is a continuation of application No. PCT/CN2018/118536, filed on Nov. 30, 2018.

(51) Int. Cl.
| | |
|---|---|
| *F16H 35/06* | (2006.01) |
| *B25J 9/10* | (2006.01) |
| *B25J 9/12* | (2006.01) |
| *B25J 17/02* | (2006.01) |
| *F16H 1/14* | (2006.01) |
| *F16H 1/20* | (2006.01) |

(52) U.S. Cl.
CPC ............... *B25J 9/102* (2013.01); *B25J 9/126* (2013.01); *B25J 17/0241* (2013.01); *B25J 17/0258* (2013.01); *F16H 1/14* (2013.01); *F16H 1/203* (2013.01); *F16H 35/06* (2013.01)

(58) Field of Classification Search
CPC .... B25J 9/146; B25J 15/0213; B25J 17/0258; B25J 9/102; B25J 9/126; B25J 17/0241; F16H 35/06; F16H 1/203; F16H 1/14
USPC .............................. 74/665 M, 385, 417, 89.13
See application file for complete search history.

(56) References Cited

FOREIGN PATENT DOCUMENTS

CN           106999251 A  *  8/2017  ............. A61B 34/30

* cited by examiner

*Primary Examiner* — Randell J Krug
(74) *Attorney, Agent, or Firm* — Baker & McKenzie LLP

(57) ABSTRACT

Embodiments relate to robotic arm assemblies. Robotic arm assembly includes an arm segment and end-effector assembly. Arm segment includes an elongated body which forms an arm segment central axis. End-effector assembly is securable to the arm segment. End-effector assembly includes an instrument assembly and first gear assembly. Instrument assembly includes an instrument and instrument gear. Instrument forms an instrument central axis. Instrument is for performing an action. Proximal end of instrument is secured to the instrument gear. First gear assembly includes a first primary gear and protrusion portion. First primary gear includes a second central axis formed through the first primary gear. Second central axis intersects with first central axis, instrument central axis, and arm segment central axis. Protrusion portion is secured to the first primary gear, and includes an opening. A portion of the proximal end of the instrument is provided in the opening and rotatable within the opening.

30 Claims, 17 Drawing Sheets

ROBOTIC ARM SYSTEM WITH GEAR-DRIVEN END-EFFECTOR ASSEMBLY

CROSS-REFERENCE TO RELATED APPLICATIONS

This application is a continuation application of U.S. application Ser. No. 16/290,402 filed Mar. 1, 2019, which is a continuation application of International Application No. PCT/CN2018/118536 filed Nov. 30, 2018, the contents of all of which are hereby expressly incorporated by reference in their entirety, including the contents and teachings of any references contained therein.

TECHNICAL FIELD

The present disclosure relates generally to robotic systems, devices, and methods for performing an action, and more specifically, relates to surgical robotic systems, devices, and methods for performing surgical actions, including, but not limited to, minimally invasive surgical (MIS) procedures, natural orifice transluminal endoscopic surgical (NOTES) procedures, etc. Example embodiments of the robotic system, device, and method can be used in a broad range of applications, industries and/or fields.

BACKGROUND

Conventionally, surgical procedures performed in a body cavity of a patient, such as the abdominal cavity, required one or more large access incisions to a patient in order for the surgical team to perform a surgical action. With advancements in medical science and technology, such conventional surgical procedures have been largely replaced by minimally invasive surgery (MIS) procedures and, where applicable, natural orifice transluminal endoscopic surgical procedures (NOTES). Recent developments in respect to computer-assisted and/or robotic surgical technology have contributed to advancements in the MIS and NOTES fields, including the ability to translate a surgeon's desired surgical actions into precise movements of surgical instruments inside a body cavity of a patient.

BRIEF SUMMARY

Despite recent developments in modern medical science and technology, it is recognized in the present disclosure that one or more problems are encountered in modern surgical technology and methodology. For example, a typical MIS procedure requires multiple incisions to a patient in order to allow access via the incisions for the insertion of a camera and various other laparoscopic instruments into the body cavity of the patient.

As another example, surgical robotic systems oftentimes face difficulties in providing, at the same time within a patient's cavity, left and right surgical robotic arms each having a main instrument (such as a cutting or gripping instrument attached to the end of a surgical robotic arm) and one or more assistant instruments (such as a gripper, retractor, suction/irrigation, and/or image capturing device).

It is also recognized in the present disclosure that surgical robotic systems face difficulties in providing an instrument, such as a cutting or gripping instrument attached to the end of a surgical robotic arm, with access to all or even most parts, areas, and/or quadrants of abdominal cavity of a patient. That is, after the surgical robotic arm is inserted in the abdominal cavity of the patient and ready to perform a surgical action, the instrument attached to the end of the surgical robotic arm is typically limited to access only certain parts, areas, and quadrants of the abdominal cavity of the patient.

In yet another example, known surgical robotic systems typically provide only between one to two surgical robotic arms per access or opening (such as an incision or a natural orifice) of the patient. In this regard, one or more additional incisions will be required for the insertion of a camera and various laparoscopic instruments into the abdominal cavity of the patient.

Present example embodiments relate generally to and/or comprise systems, subsystems, processors, devices, logic, and methods for addressing conventional problems, including those described above.

In an exemplary embodiment, a robotic arm assembly is disclosed. The robotic arm assembly may include an arm segment and an end-effector assembly. The arm segment may include an elongated body with proximal and distal ends. The elongated body of the arm segment may form an arm segment central axis. The arm segment may further include a first motor having a first drive portion and a second motor having a second drive portion. The end-effector assembly may be configurable to be securable to the distal end of the arm segment. The end-effector assembly may include an instrument assembly, a first gear assembly, and a second gear assembly. The instrument assembly may include an instrument and an instrument gear. The instrument may include an elongated body with a proximal end and a distal end. The elongated body of the instrument may form an instrument central axis. The distal end of the instrument may be used to perform an action (e.g., a surgical action). The proximal end of the instrument may include a first section and a second section separate from the first section. The first section and the instrument gear may be fixedly secured relative to one another in such a way that, when one of the first section or the instrument gear is driven to rotate in a first direction relative to a first central axis formed through the instrument gear, the distal end of the instrument and the other one of the first section or the instrument gear may be driven to rotate in the first direction relative to the first central axis. The first central axis may be orthogonal to the instrument central axis. The first gear assembly may be configurable to be driven by the first drive portion of the first motor. The first gear assembly may include a first primary gear and a protrusion portion. The first primary gear may have a second central axis formed through the first primary gear. The second central axis may intersect with the first central axis, the instrument central axis, and the arm segment central axis. The second central axis and the first central axis may be orthogonal to each other at all times, and the second central axis and the arm segment central axis may be orthogonal to each other at all times. The protrusion portion may be configurable to be secured to a surface of the first primary gear. The protrusion portion may include a protrusion portion opening formed along the first central axis. The protrusion portion opening may be fixedly positioned relative to the instrument assembly such that a center axis of the protrusion portion opening is aligned with the first central axis. The protrusion portion and the instrument assembly may be collectively configured in such a way that the second section of the proximal end of the instrument is provided in the protrusion portion opening and rotatable within the protrusion portion opening. When the instrument gear is driven to rotate in the first direction relative to the first central axis, the protrusion portion opening and the second section of the proximal end of the instrument may be collectively configured so as to allow the second section of the proximal end of the instrument that is provided in the protrusion portion opening to rotate in the first direction relative to the first central axis. The second gear assembly may be configurable to be driven by the second drive portion of the second motor. The second gear assembly may include a second primary gear. The second primary gear may be positioned in such a way that its central axis is aligned with the second central axis. The second primary gear may be configurable to drive the instrument gear to rotate. When the second primary gear is driven by the second drive portion of the second motor to rotate in a second direction relative to the second central axis and the first primary gear is not driven by the first drive portion of the first motor to rotate, the second primary gear may be configured to drive the instrument gear to rotate in the first direction relative to the first central axis. When the second primary gear is not driven by the second drive portion of the second motor to rotate and the first primary gear is driven by the first drive portion of the first motor to rotate in a third direction relative to the second central axis, the third direction opposite to the second direction, the first primary gear may be configured to drive the instrument gear to rotate in the first direction relative to the first central axis. When the first and second primary gears are both driven by the first and second drive portions, respectively, to rotate at the same rotational rate in the same second direction relative to the second central axis, the first and second primary gears may be configured to prevent the instrument gear from rotating relative to the first central axis.

In another exemplary embodiment, a robotic arm assembly is disclosed. The robotic arm assembly may include an end-effector assembly. The end-effector assembly may include an instrument assembly, a first gear assembly, and a second gear assembly. The instrument assembly may include an instrument, an instrument gear, and an instrument assembly body between the instrument and the instrument gear. The instrument may include an elongated body with a proximal end and a distal end. The elongated body of the instrument may form an instrument central axis. The distal end of the instrument may be used to perform an action (e.g., surgical action). The instrument, the instrument gear, and the instrument assembly body may be fixedly secured relative to one another in such a way that a rotation of the instrument gear in a first direction relative to a first central axis formed through the instrument gear drives the distal end of the instrument to corresponding rotate in the first direction relative to the first central axis. The first central axis and the instrument central axis may be always orthogonal to each other. The first gear assembly may include a first primary gear. The first primary gear may have a protrusion portion and a second central axis formed through the first primary gear. The protrusion portion may include a protrusion portion opening fixedly positioned relative to the instrument assembly in such a way that a center axis of the protrusion portion opening is aligned with the first central axis. The protrusion portion and the instrument assembly may be collectively configured in such a way that a portion of the instrument assembly body is provided in the protrusion portion opening, rotatable relative to the first central axis, and rotatable within the protrusion portion opening, The second central axis may intersect with the first central axis of the instrument central axis. The second central axis and the first central axis may be orthogonal to each other at all times. The second gear assembly may include a second primary gear. The second primary gear may be positioned in such a way that its central axis is aligned with the second central axis. The second primary gear may be configured to be interlocking with the instrument gear so as to drive the instrument gear to rotate when the second primary gear rotate.

In another exemplary embodiment, a robotic arm assembly is disclosed. The robotic arm assembly may include an arm segment and an end-effector assembly. The arm segment may include an elongated body with proximal and distal ends, a first motor having a first drive portion, a second motor having a second drive portion and a third motor having a third drive portion. The elongated body of the arm segment may form an arm segment central axis. The end-effector assembly may be securable to the distal end of the arm segment. The end-effector assembly may include an instrument assembly, a first gear assembly, a second gear assembly, and a third gear assembly. The instrument assembly may include an instrument and an instrument gear. The instrument may include an elongated body with a proximal end and a distal end. The elongated body of the instrument may form an instrument central axis. The distal end of the instrument may have a first member and a second member for use in performing an action (e.g., surgical action). The proximal end of the instrument may include a first section and a second section separate from the first section. The first section and the instrument gear may be fixedly secured relative to one another in such a way that, when one of the first section or the instrument gear is driven to rotate in a first direction relative to a first central axis formed through the instrument gear, the distal end of the instrument and the other one of the first section or the instrument gear may be driven to rotate in the first direction relative to the first central axis. The first central axis may be orthogonal to the instrument central axis. The first gear assembly may be configurable to be driven by the first drive portion of the first motor. The first gear assembly may include a first primary gear and a protrusion portion. The first primary gear may have a second central axis formed through the first primary gear. The second central axis may intersect with the first central axis, the instrument central axis, and the arm segment central axis. The second central axis and the first central axis may be always orthogonal to each other at all times. The second central axis and the arm segment central axis may be always orthogonal to each other. The protrusion portion may be configurable to be secured to a surface of the first primary gear. The protrusion portion may include a protrusion portion opening formed along the first central axis. The protrusion portion and the instrument assembly may be collectively configured in such a way that the second section of the proximal end of the instrument is provided in the protrusion portion opening and rotatable within the protrusion portion opening. When the instrument gear is driven to rotate in the first direction relative to the first central axis, the protrusion portion opening and the second section of the proximal end of the instrument may be collectively configured so as to allow the second section of the proximal end of the instrument that is provided in the protrusion portion opening to rotate in the first direction relative to the first central axis. The second gear assembly may be configurable to be driven by the second drive portion of the second motor. The second gear assembly may include a second primary gear. The second primary gear may be positioned in such a way that its central axis is aligned with the second central axis. The second primary gear may be configurable to drive the instrument gear to rotate. The third gear assembly may be configurable to be driven by the third drive portion of the third motor. The third gear assembly may be configurable to drive the first member and/or the second member to move relative to the instrument central axis.

In another exemplary embodiment, a robotic arm assembly is disclosed. The robotic arm assembly includes an arm segment and an end-effector assembly. The arm segment includes an elongated body with proximal and distal ends. The elongated body of the arm segment forms an arm segment central axis. The end-effector assembly is securable to the distal end of the arm segment. The end-effector assembly includes an instrument assembly and a first gear assembly. The instrument assembly includes an instrument and an instrument gear. The instrument includes an elongated body with a proximal end and a distal end. The elongated body of the instrument forms an instrument central axis. The distal end of the instrument is for use in performing an action. The proximal end of the instrument is fixedly secured to the instrument gear in such a way that, when the instrument gear is driven to rotate in a first direction relative to a first central axis formed through the instrument gear, the distal end of the instrument is driven to rotate in the first direction relative to the first central axis. The first gear assembly includes a first primary gear and a protrusion portion. The first primary gear includes a second central axis formed through the first primary gear. The second central axis intersects with the first central axis, the instrument central axis, and the arm segment central axis. The second central axis and the first central axis are always orthogonal to each other. The second central axis and the arm segment central axis are always orthogonal to each other. The protrusion portion is secured to the first primary gear. The protrusion portion includes a protrusion portion opening. The protrusion portion and the instrument assembly are collectively configured in such a way that at least a portion of the proximal end of the instrument is provided in the protrusion portion opening and rotatable within the protrusion portion opening.

In another exemplary embodiment, a robotic arm assembly is disclosed. The robotic arm assembly includes an end-effector assembly. The end-effector assembly includes an instrument assembly and a first gear assembly. The instrument assembly includes an instrument, an instrument gear, and an instrument assembly body between the instrument and the instrument gear. The instrument includes an elongated body with a proximal end and a distal end. The elongated body of the instrument forms an instrument central axis. The distal end of the instrument is for use in performing an action. The instrument, the instrument gear, and the instrument assembly body are fixedly secured relative to one another in such a way that a rotation of the instrument gear in a first direction relative to a first central axis formed through the instrument gear drives the distal end of the instrument to correspondingly rotate in the first direction relative to the first central axis. The first central axis and the instrument central axis are always orthogonal to each other. The first gear assembly includes a first primary gear. The first primary gear includes a protrusion portion and a second central axis formed through the first primary gear. The protrusion portion includes a protrusion portion opening fixedly positioned relative to the instrument assembly in such a way that a center axis of the protrusion portion opening is aligned with the first central axis. The protrusion portion and the instrument assembly are collectively configured in such a way that a portion of the instrument assembly body is provided in the protrusion portion opening and rotatable within the protrusion portion opening. The second central axis intersects with the first central axis of the instrument central axis. The second central axis and the first central axis are always orthogonal to each other.

In another exemplary embodiment, a robotic arm assembly is disclosed. The robotic arm assembly includes an arm segment and an end-effector assembly. The arm segment includes an elongated body with proximal and distal ends. The elongated body of the arm segment forms an arm segment central axis. The end-effector assembly is securable to the distal end of the arm segment. The end-effector assembly includes an instrument assembly and a first gear assembly. The instrument assembly includes an instrument and an instrument gear. The instrument includes an elongated body with a proximal end and a distal end. The elongated body of the instrument forms an instrument central axis. The distal end of the instrument includes a first member and a second member for use in performing an action. The proximal end of the instrument is fixedly secured to the instrument gear in such a way that, when the instrument gear is driven to rotate in a first direction relative to a first central axis formed through the instrument gear, the distal end of the instrument is driven to rotate in the first direction relative to the first central axis. The first central axis is orthogonal to the instrument central axis. The first gear assembly includes a first primary gear and a protrusion portion. The first primary gear includes a second central axis formed through the first primary gear. The second central axis intersects with the first central axis, the instrument central axis, and the arm segment central axis. The second central axis and the first central axis are always orthogonal to each other. The second central axis and the arm segment central axis are always orthogonal to each other. The protrusion portion is secured to the first primary gear. The protrusion portion includes a protrusion portion opening. The protrusion portion and the instrument assembly are collectively configured in such a way that the proximal end of the instrument is provided in the protrusion portion opening and rotatable within the protrusion portion opening.

BRIEF DESCRIPTION OF THE DRAWINGS

For a more complete understanding of the present disclosure, example embodiments, and their advantages, reference is now made to the following description taken in conjunction with the accompanying drawings, in which like reference numbers indicate like features, and.

Although similar reference numbers may be used to refer to similar elements in the figures for convenience, it can be appreciated that each of the various example embodiments may be considered to be distinct variations.

Figure 1:
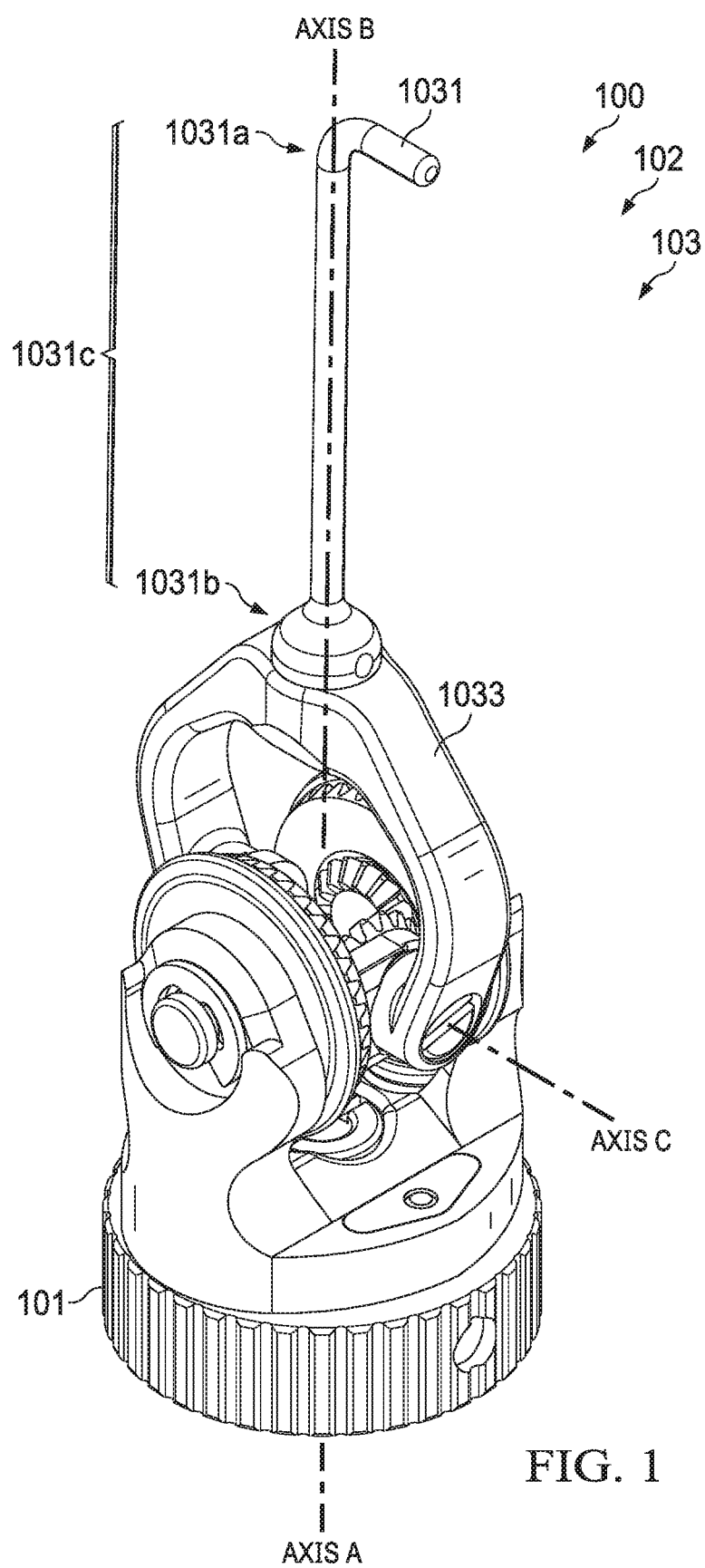
FIG. 1 is an illustration of a perspective view of an example embodiment of a robotic arm assembly.

Example embodiments will now be described with reference to the accompanying drawings, which form a part of the present disclosure and which illustrate example embodiments which may be practiced. As used in the present disclosure and the appended claims, the terms "embodiment," "example embodiment," "exemplary embodiment," and "present embodiment" do not necessarily refer to a single embodiment, although they may, and various example embodiments may be readily combined and/or interchanged without departing from the scope or spirit of example embodiments. Furthermore, the terminology as used in the present disclosure and the appended claims is for the purpose of describing example embodiments only and is not intended to be limitations. In this respect, as used in the present disclosure and the appended claims, the term "in" may include "in" and "on," and the terms "a," "an," and "the" may include singular and plural references. Furthermore, as used in the present disclosure and the appended claims, the term "by" may also mean "from," depending on the context. Furthermore, as used in the present disclosure and the appended claims, the term "if" may also mean "when" or "upon," depending on the context. Furthermore, as used in the present disclosure and the appended claims, the words "and/or" may refer to and encompass any and all possible combinations of one or more of the associated listed items.

DETAILED DESCRIPTION

Despite recent developments in medical science and technology, problems continue to exist in modern surgical technology and methodology, including those pertaining to MIS and NOTES. For example, a typical MIS procedure will generally require a surgeon to perform multiple incisions to a patient in order to enable the surgeon to insert, via such incisions, required laparoscopic instruments into the body cavity of the patient. Furthermore, it is recognized herein that a significant technical challenge encountered when using surgical robotic systems pertains to the difficulty in establishing sufficient anchoring and/or reactive forces to react to and/or stabilize against forces that need to be applied inside the body cavity of the patient by the surgical robotic system during a surgical action. In this regard, the use of known systems to perform certain surgical actions may require tremendous effort and time, and eventually may not be performed properly or at all due to such insufficient anchoring and/or reactive forces. Furthermore, surgeons using known surgical systems often encounter problems in respect to utilizing an instrument, such as a cutting and/or gripping instrument attached to the end of a surgical robotic arm, in certain parts, areas, and quadrants of a body cavity (such as an abdomen) of a patient after the system has been set up (or anchored) and ready to perform surgery. That is, after the surgical robotic arm of the system has been inserted and properly set up in the abdominal cavity of a patient, the surgical instrument attached to the end of the surgical robotic arm is typically mechanically limited to accessing only certain parts, areas, and quadrants of the abdominal cavity of the patient.

Known surgical robotic system also oftentimes face problems in achieving maximum flexibility, better visualization and greater range of motion of the instrument, and improving ergonomics for the surgeons.

Surgical systems, devices, and methods, including those for use in MIS and NOTES, are described in the present disclosure. It is to be understood in the present disclosure that the principles described herein may be applied outside of the context of MIS and/or NOTES, such as performing scientific experiments and/or procedures in environments that are not readily accessible by humans, including in a vacuum, in outer space, and/or under toxic and/or dangerous conditions, without departing from the teachings of the present disclosure.

The Robotic Arm Assembly (e.g., Robotic Arm Assembly 100, 200, 300).

FIG. 1 illustrates an example embodiment of a robotic arm assembly (e.g., robotic arm assembly 100, 200, 300) configurable or configured for use in performing an action or procedure. Although example actions or procedures in the present disclosure may be directed to or reference example applications pertaining to surgical actions or procedures, it is to be understood in the present disclosure that example embodiments of the robotic arm assembly may be used in other actions or procedures, including non-surgical actions and/or procedures, without departing from the teachings of the present disclosure. One or more robotic arm assemblies 100, 200, 300 may be securable or secured to a surgical system (not shown).

Each robotic arm assembly 100, 200, 300 may be configurable or configured to be inserted into a cavity (e.g., an abdominal cavity) of a patient via a single access or opening (e.g., a single incision (such as an incision in or around the umbilical area) or via a natural orifice (such as a rectum or vagina, for performing natural orifice transluminal endoscopic surgery (or NOTES), hereinafter referred to as an "opening")) of the patient. For example, the surgical system may include a port assembly (not shown). The port assembly may be an elongated cylindrical-shaped body having a main access channel formed through the elongated body and a plurality of anchor portions. The port assembly may be inserted into an incision or opening of a patient so as to create an access channel and anchor point for the one or more robotic arm assemblies 100, 200, 300 to be inserted, via the main access channel of the port assembly, into a cavity of a patient and anchored, via one or more of the anchor portions of the port assembly, to the port assembly.

One or more of the robotic arm assemblies (e.g., robotic arm assembly 100, 200, 300) may include a configurable or configured serial (or linear) arrangement of a plurality of arm segments, including arm segment (e.g., arm segment 101), joint portions, and at least one end-effector assembly (e.g., end-effector assembly 202, 302). One or more of the robotic arm assemblies (e.g., robotic arm assembly 100, 200, 300), or elements thereof, may include integrated haptic and/or force feedback subsystems (not shown) configurable or configured to provide to a haptic feedback response to a user interface (e.g., a user interface for use by a surgeon or assistant), and such haptic feedback response may be first processed by a controller (not shown).

The one or more surgical arm assemblies (e.g., robotic arm assembly 100, 200, 300) may also be configurable or configured to provide the controller and/or user interface with one or more of a plurality of feedback responses and/or measurements, including those pertaining to position (including orientation), applied force, proximity, temperature, pressure, humidity, etc., of, by, and/or nearby to the robotic arm assembly (e.g., robotic arm assembly 100, 200, 300). In addition to the haptic feedback response, the controller may be further configurable or configured to, among other things, translate, replicate, map, and/or sense the delicate movements of the operator using the user interface into movements of the robotic arm assembly (e.g., robotic arm assembly 100, 200, 300) with high precision, high dexterity, and minimum burden.

One or more of the robotic arm assemblies (e.g., robotic arm assembly 100, 200, 300) may also be configurable or configured to receive an electric current (or voltage potential, thermal energy, heat, cold temperature application, etc.) from an energy source (or other source, not shown).

In example embodiments, an energy source (or other source) may also be integrated, in part or in whole, into one or more of the robotic arm assemblies (e.g., robotic arm assembly 100, 200, 300). An electrical current (or voltage potential, thermal energy, heat, or cold temperature application) from the energy source (or other source) may be selectively applied to one or more elements of the end-effector assembly (e.g., end-effector assembly 102, 202, 302), and such selective application of the electric current (or voltage potential, thermal energy, heat, cold temperature application, etc.) may be configured and/or controlled by the user interface (e.g., via the controller). For example, in situations wherein the end-effector assembly (e.g., end-effector assembly 102) includes one instrument (e.g., a cautery hook, etc.), an operator of the user interface may configure the user interface to command (e.g., via the controller) the energy source (or other source) to apply the electric current (or voltage potential, thermal energy, heat, cold temperature application, etc.) to the one instrument. As another example, in situations wherein the end-effector assembly (e.g., end-effector assembly 202, 302) includes a first instrument and a second instrument (e.g., the two instruments that form a grasper, cutter, etc.), an operator of the user interface may configure the user interface to command (e.g., via the controller) the energy source (or other source) to apply the electric current (or voltage potential, thermal energy, heat, cold temperature application, etc.) to the first instrument or the second instrument. It is recognized in the present disclosure that the application of such electric current (or voltage potential, thermal energy, heat, cold temperature application, etc.) to the first instrument alone or in collective operation with second instrument enables the end-effector assembly (e.g., end-effector assembly 102, 202, 302) to perform the actions of an electrosurgical instrument, or the like.

These and other elements and example embodiments of the surgical system and robotic arm assembly (e.g., robotic arm assembly 100, 200, 300) will now be further described with reference to the accompanying figures.

As illustrated in FIGS. 1-12, example embodiments of robotic arm assembly 100, 200, 300 may include one or more arm segments (e.g., arm segment 101) and one or more end-effector assemblies 102, 202, 302.

The Arm Segment (e.g., Arm Segment 101).

In an example embodiment, each arm segment 101 may be secured to and detachable from the end effector assembly (e.g., end effector assembly 102, 202, 302). The arm segment 101 may have an elongated body resembling a forearm (i.e., a portion of an arm between an elbow and a hand). The elongated body may have a proximal end (e.g., the end that is nearest to an elbow or furthest from the end effector assembly) and a distal end (e.g., the end that is furthest from the elbow or nearest to the end effector assembly). The elongated body may form an arm segment central axis (e.g., axis A illustrated in at least FIG. 1). The arm segment 101, including the end-effector assembly 102, 202, 302 when the end effector assembly 102, 202, 302 is secured to the arm segment 101, may be rotatable relative to the arm segment central axis (e.g., a roll movement relative to axis A).

The arm segment 101 may include one or more joint portions and/or wrist portions (not shown) for use in enabling the end effector assembly 102, 202, 302 to detach from and secure to the distal end of the arm segment 101.

It is to be understood in the present disclosure that the arm segment 101 may be secured to a second arm segment (not shown) via one or more second joint portions and/or elbow portions (not shown). For example, the proximal end of the first arm segment 101 may be secured to a distal end of the second arm segment via a second joint portion to enable, among other things, the distal end of the arm segment 101 to pivot, move, and/or rotate relative to one or more of the second joint portions (or relative to a distal end of the second arm segment). As another example, the proximal end of the first arm segment 101 may be secured to the distal end of the second arm segment via a second joint portion to enable the arm segment 101 to rotate relative to the arm segment central axis (e.g., a roll movement relative to axis A). It is also to be understood in the present disclosure that the second arm segment may be secured to a third arm segment (not shown) resembling a shoulder. The second arm segment may be secured to the third arm segment via one or more third joint portions and/or shoulder portions (not shown). For example, a proximal end of the second arm segment may be secured to a distal end of the third arm segment to enable, among other things, the distal end of the second arm segment to pivot, move, and/or rotate relative to one or more of the third joint portions (or relative to a distal end of the third arm segment). As another example, the proximal end of the second arm segment may be secured to the distal end of the third arm segment via a third joint portion to enable the second arm segment to rotate relative to a central axis formed by the elongated body of the second arm segment.

Figure 2A:
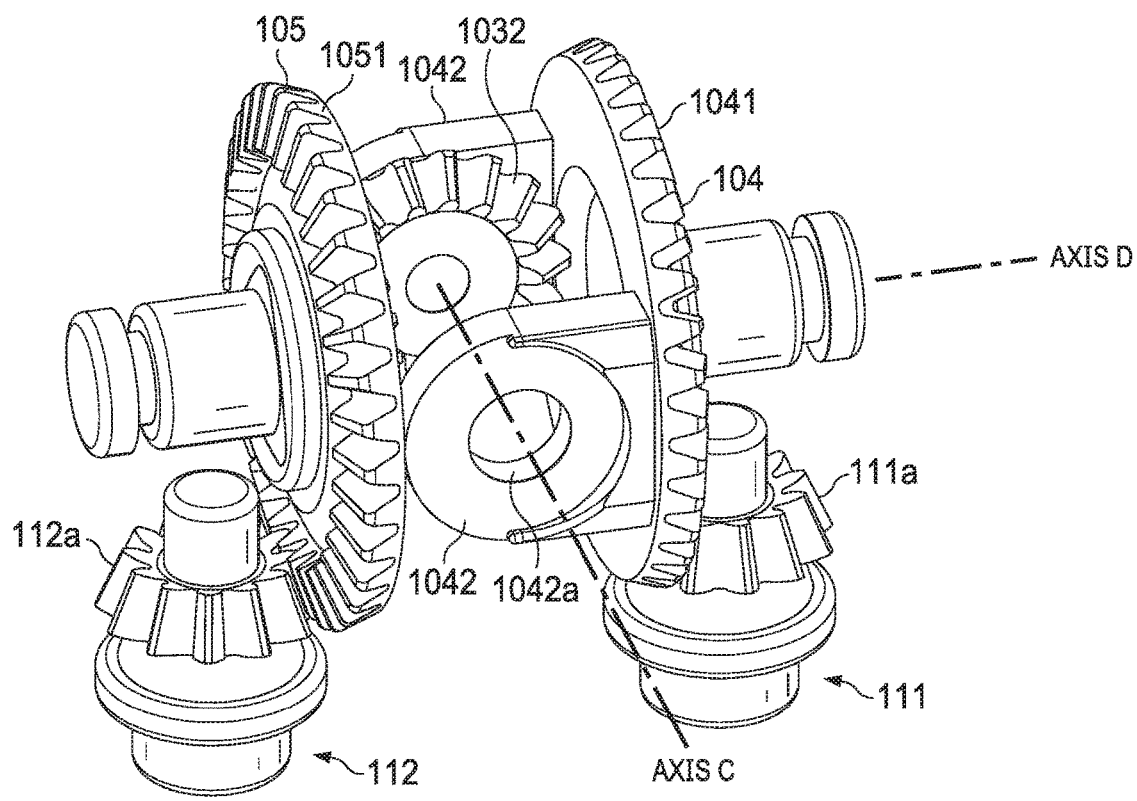
FIG. 2A is an illustration of a perspective view of an example embodiment of the first gear assembly and the second gear assembly.
Figure 2B:
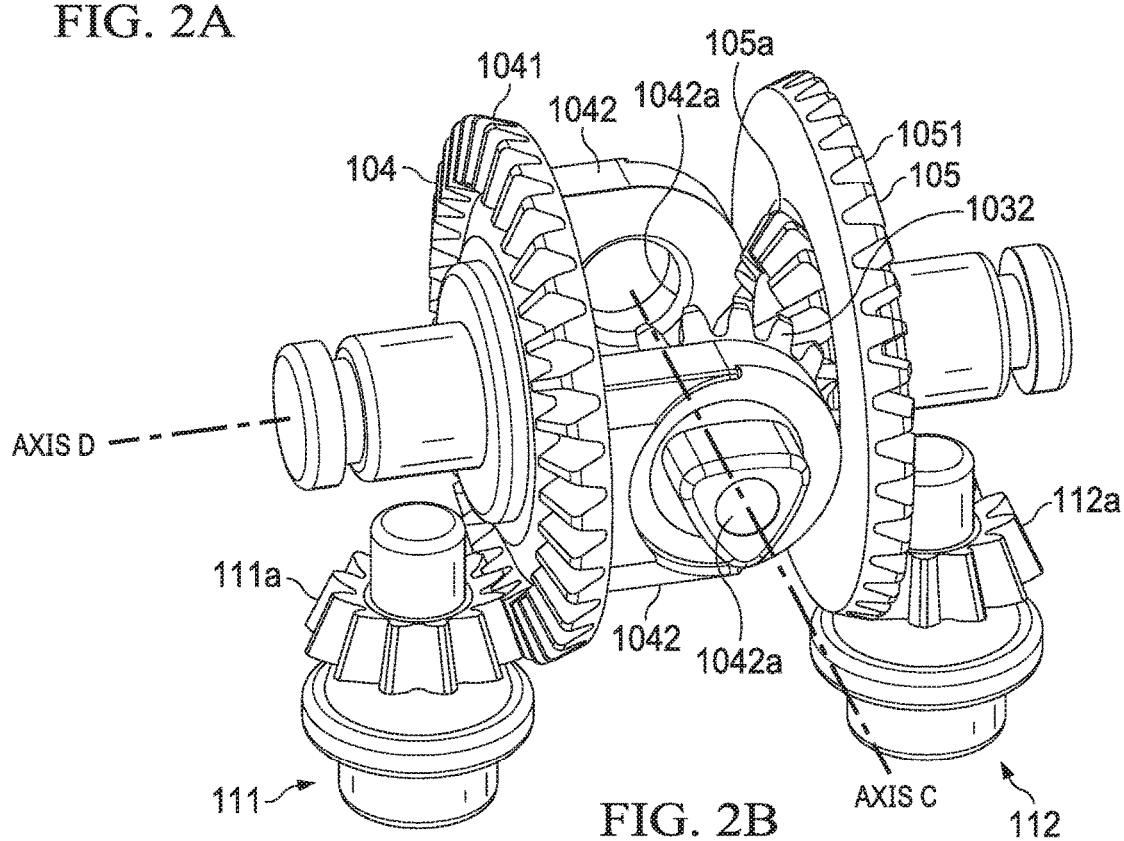
FIG. 2B is an illustration of another perspective view of an example embodiment of the first gear assembly and second gear assembly.
Figure 3:
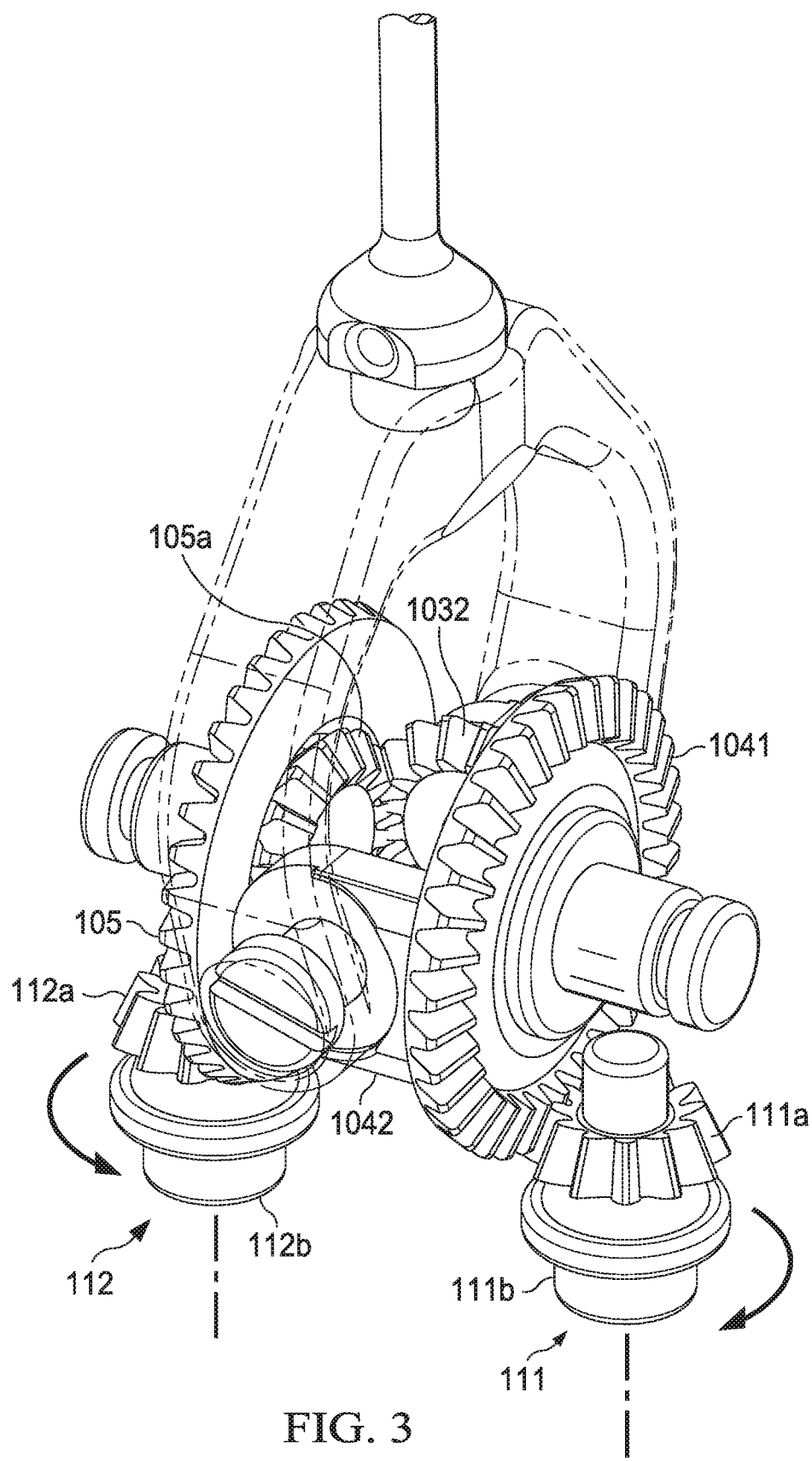
FIG. 3 is an illustration of a perspective view of an example embodiment of the first gear assembly, the second gear assembly, and the end-effector assembly.

The arm segment 101 may include one or more integrated motors housed within the elongated body of the arm segment 101. FIG. 2A, FIG. 2B, and FIG. 3 illustrate an example embodiment of a robotic arm assembly configurable or configured with a first motor 111 and a second motor 112. The first motor 111 may include a first drive portion 111*a* and a first drive shaft 111*b*. The first drive portion 111*a* of the first motor 111 may be configurable or configured to rotate relative to the first drive shaft 111*b*. The second motor 112 may have a second drive portion 112*a* and a second drive shaft 112*b*. The second drive portion 112*a* of the second motor 111 may be configurable or configured to rotate relative to the second drive shaft 112*b*. In an example embodiment, the first motor 111 and the second motor 112 may be securely housed to be parallel with each other within the elongated body of the arm segment 101 in such a way that the first drive shaft 111*b* of the first motor 111 and the second drive shaft 112*b* of the second motor 112 are parallel with each other and the first drive portion. In an example embodiment, the first drive portion 111*a* and the second drive portion 112*a* may be or include one or more gears, or the like. The gears of the first drive portion 111*a* and the second drive portion 112*a* may be configured to have the same profile and parameters, for example, same diameter, same numbers/sizes of teeth, teeth depth/thickness, same gear ratio, same speed ratio and/or same face width. It is to be understood in the present disclosure that the gears of the first drive portion 111*a* and the second drive portion 112*a* may be configured to have different profiles and/or parameters without departing from the teachings of the present disclosure. Although the figures illustrate an arm segment having a first motor 111 and a second motor 112, it is to be understood in the present disclosure that the arm segment may have more other drive portion without departing from the teachings of the present disclosure. It is also to be understood that in the present disclosure that the drive portion may be arranged in a non-parallel way and the gears may not have same profile and/or parameters. In addition, other driven methods such as friction-driven mechanism may also be used in addition to or in replacement of the gears described above and in the present disclosure without departing from the teachings of the present disclosure.

The End-Effector Assembly (e.g., End-Effector Assembly 102).

FIGS. 1-14 illustrate an example embodiment of a robotic arm assembly 100 having an end-effector assembly (e.g., end-effector assembly 102). The end-effector assembly 102 may be securable or secured to the distal end of the arm segment 101. In an example embodiment, the end-effector assembly 102 may be secured to and detached from the distal end of the arm segment 101. The end-effector assembly 102 may include an instrument assembly (e.g., instrument assembly 103). The end-effector assembly 102 may also include a first gear assembly (e.g., first gear assembly 104). The end-effector assembly 102 may also include a second gear assembly (e.g., second gear assembly 105). These and other elements of the end-effector assembly 102 will now be described with reference to the accompanying drawings.

(i) Instrument Assembly (e.g., Instrument Assembly 103).

As illustrated in at least FIG. 1, FIG. 3, FIG. 4A, FIG. 4B, FIG. 4C, and FIG. 4D, an example embodiment of the end-effector assembly 102 may include an instrument assembly (e.g., instrument assembly 103). The instrument assembly 103 may include an instrument (e.g., instrument 1031) for use in performing a surgical action or procedure. Although the figures may illustrate an end-effector assembly 102 having instrument assembly 103 with one instrument 1031, it is to be understood in the present disclosure that the end-effector assembly 102 may have different instrument assemblies, such as instrument assemblies having more than one instrument (e.g., instrument assembly 203 or 303, as described in the present disclosure) and/or instrument assemblies with different single instruments (e.g., instruments 1031 that are straight instruments with or without a hook at its distal end) without departing from the teachings of the present disclosure.

The instrument assembly 103 may also include one or more instrument gears 1032, or the like. For example, the instrument assembly 103 may include one instrument gear 1032, as illustrated in at least FIGS. 2A, 2B, 3, 4A-D, 6, 7, and 10. As another example, the instrument assembly 103 may include two instrument gears (not shown). In such an example, one instrument gear may be connected to segment 1033*a* of the intermediary instrument section 1033 and another instrument gear may be connected to another segment 1033*b* of the intermediary instrument section 1033.

The instrument 1031 may include an elongated body with a proximal end 1031*b* and a distal end 1031*a*. The distal end 1031*a* of the instrument 1031 may include a bended or curved portion 1031*a* (e.g., the cautery hook illustrated in at least FIGS. 1 and 5-8). Alternatively, the instrument 1031 may be a continuously straight elongated body, such as the instrument 1031 illustrated in at least FIGS. 4A-D. Other configurations, shapes, and/or sizes of the instrument 1031, including the distal end 1031*a* of the instrument 1031, are contemplated without departing from the teachings of the present disclosure.

The main straight portion 1031*c* of the elongated body of the instrument 1031 from the proximal end 1031*b* of the elongated body of the instrument 1031 to the distal end 1031*a* (or bended portion 1031*a*) may form an instrument central axis (e.g., axis B illustrated in at least FIGS. 1 and 4A-D). The distal end 1031*a* of the instrument 1031 may be for use in performing a surgical action or procedure. The instrument 1031 may be any surgical instrument 1031, including a cautery hook 1031, without departing from the teachings of the present disclosure.

Figure 4A:
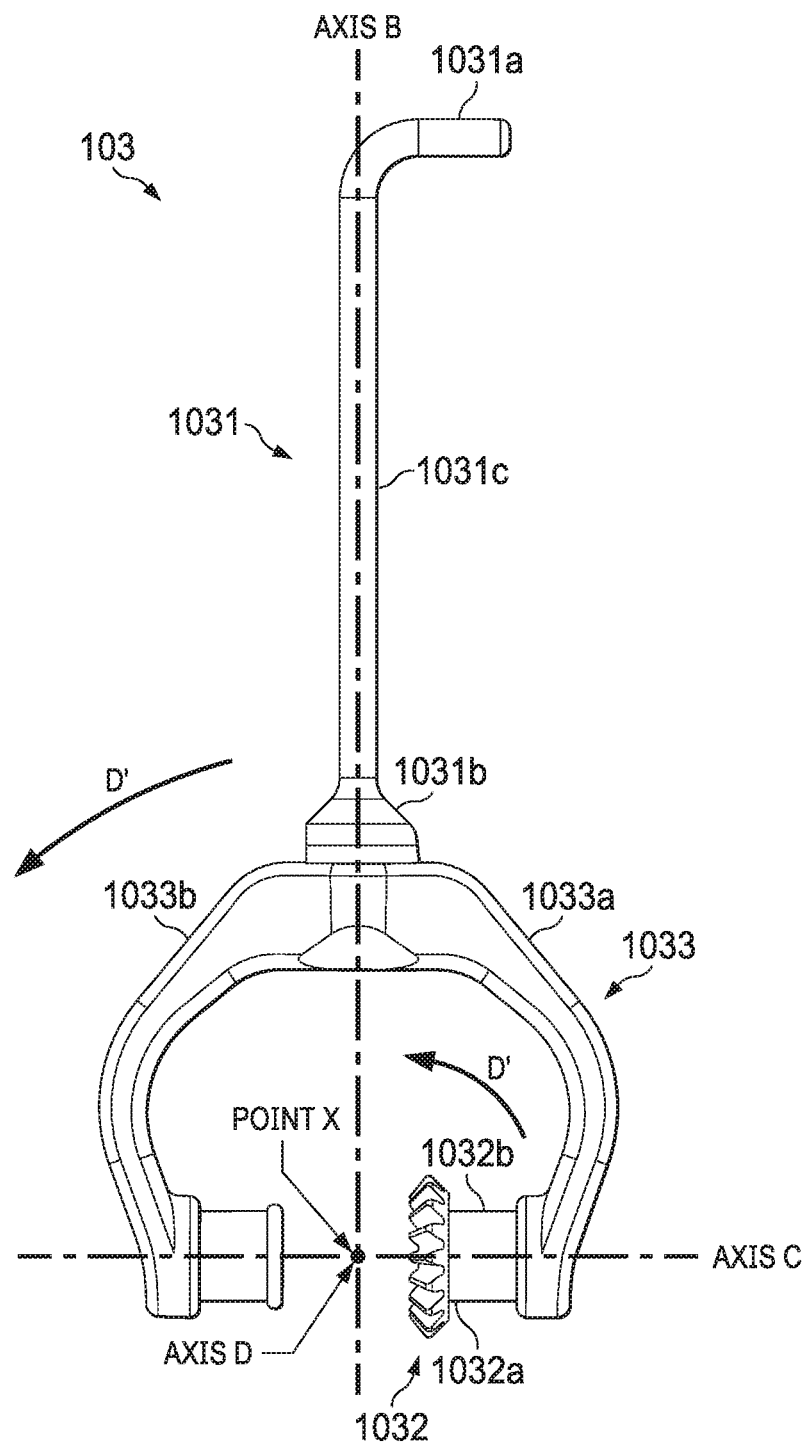
FIG. 4A is an illustration of a front view of an example embodiment of the instrument assembly.
Figure 4B:
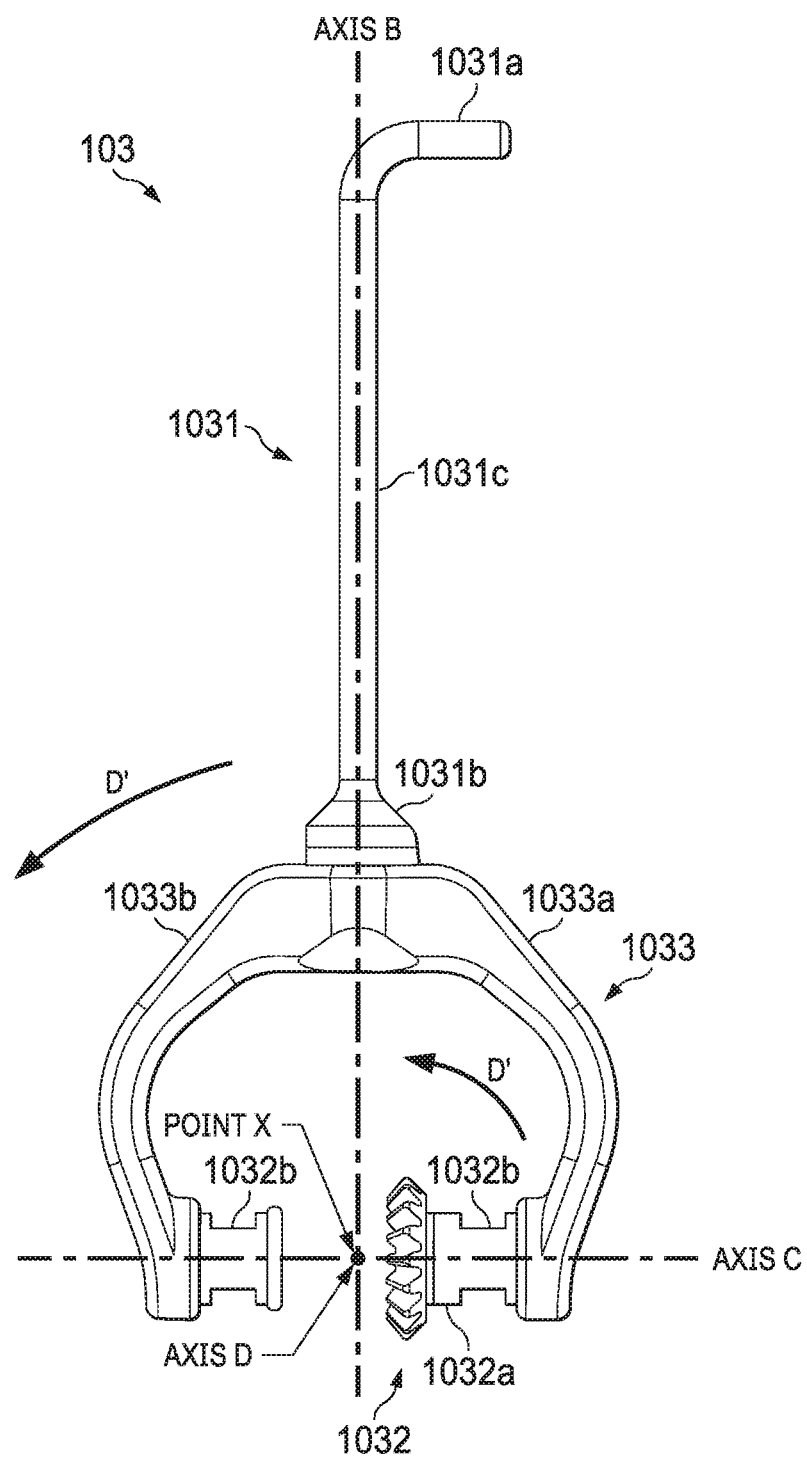
FIG. 4B is an illustration of a front view of another example embodiment of the instrument assembly.
Figure 4C:
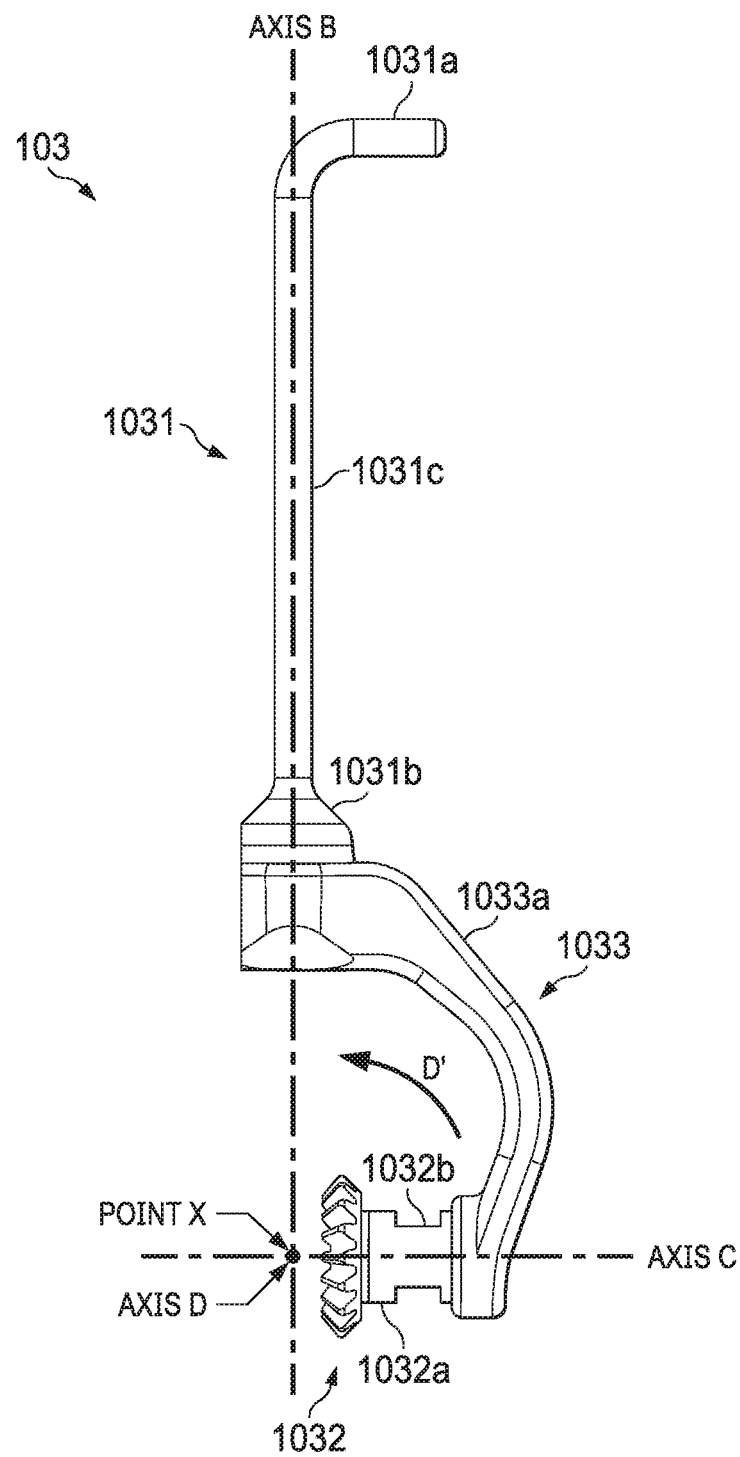
FIG. 4C is an illustration of a front view of another example embodiment of the instrument assembly.
Figure 4D:
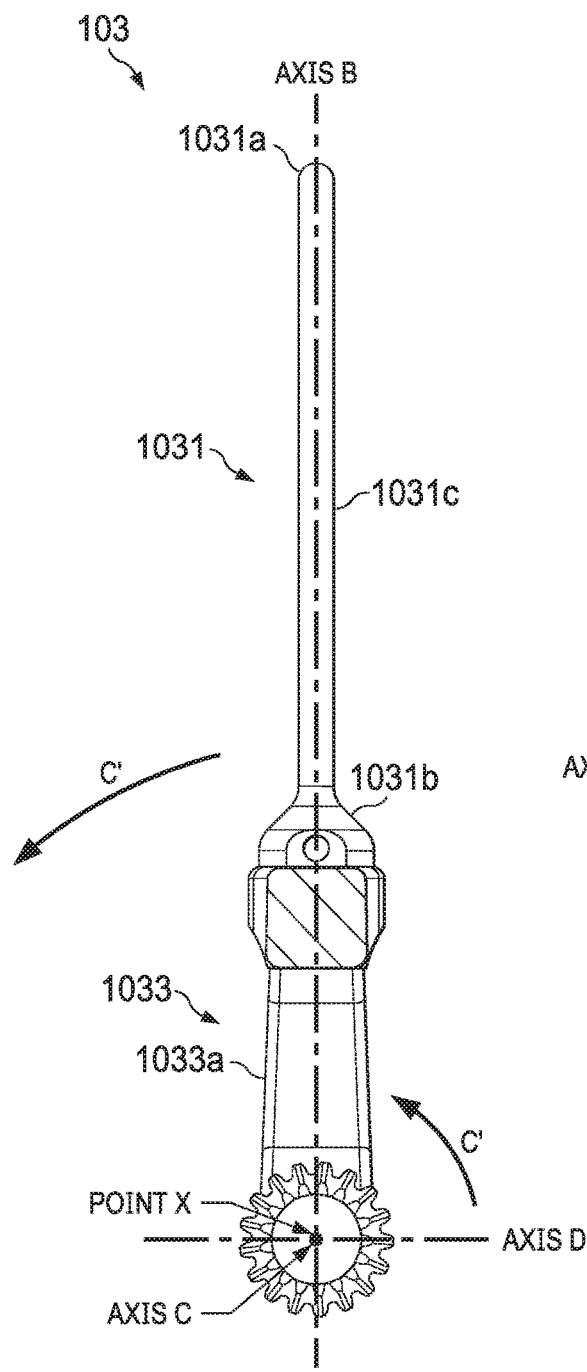
FIG. 4D is an illustration of a cross-sectional side view of an example embodiment of the instrument assembly.
Figure 4E:
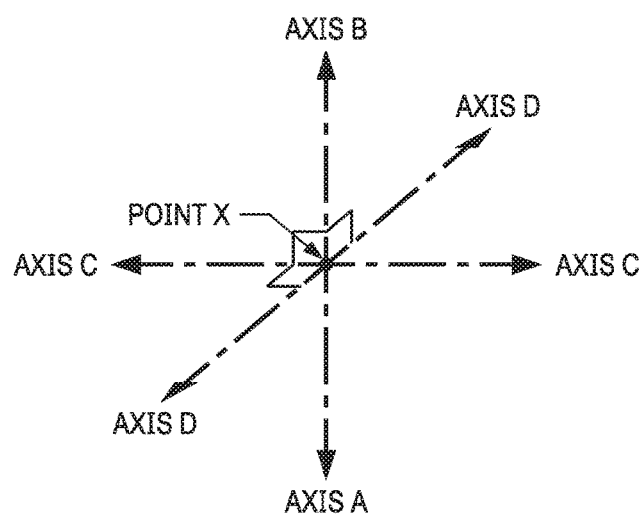
FIG. 4E is an illustration of an example relationship between the first central axis C, second central axis D, and instrument central axis B, and a point of intersection X of such axes.

The instrument assembly 103 may include a first section (e.g., first section 1032*a* illustrated in at least FIGS. 4A-C) and a second section (e.g., second section 1032*b* illustrated in at least FIGS. 4A-C). The second section 1032*b* may be separate from the first section 1032*a* (e.g., see FIGS. 4B-C) or may not be separate from the first section 1032*a* (e.g., see FIG. 4A). In example embodiments, the first section 1032*a* and second section 1032*b* may be formed as (or considered as) part of the instrument 1031. In other example embodiments, the first section 1032*a* and/or second section 1032*b* may be formed as (or considered as) separate from the instrument 1031.

The instrument assembly 103 may include an intermediary instrument section (e.g., intermediary instrument section 1033 (also referred to herein as the "instrument assembly body" 1033). In example embodiments, the intermediary instrument section 1033 may be posited between the instrument 1031 and the instrument gear 1032. In example embodiments, the intermediary instrument section 1033 may be formed as (or considered as) part of the instrument 1031. In other example embodiments, the intermediary instrument section 1033 may be formed as (or considered as) separate from the instrument 1031. The intermediary instrument section 1033 may include one or more "arms" or segments 1033*a*, 1033*b*, and/or be formed in any way, shape, and/or form such as a C-shaped body, U-shaped body, V-shaped body, J-shaped body, L-shaped body, or the like. In an example embodiment, the intermediary instrument section 1033 may be configured to provide a connection between the main straight portion 1031c (via the proximal end 1031b) of the elongated body of the instrument 1031 (which forms the instrument central axis, or axis B) and the first section 1032a and/or second section 1032b. In example embodiments, the first section 1032a and/or second section 1032b may be formed as (or considered as) part of the intermediary instrument section 1033. The first section 1032a and/or the second section 1032b may be formed along a first central axis (e.g., axis C, as illustrated in at least FIGS. 4A-C).

As illustrated in at least FIGS. 4A-C, example embodiments of the first section 1032a may be a section or part of the intermediary instrument section 1033 that is fixedly secured or connected to the instrument gear 1032 in such a way that, when either the first section 1032a or the instrument gear 1032 is driven to rotate in a first direction (e.g., direction C' illustrated in at least FIG. 4D) relative to the first central axis (e.g., axis C formed through the instrument gear 1032, as illustrated in at least FIGS. 4A-D), both the distal end 1031a of the instrument 1031 and the other one of the first section 1032a or the instrument gear 1032 are also driven to rotate in the first direction (e.g., direction C' illustrated in at least FIG. 4D) relative to the first central axis (e.g., axis C). As a more specific example, if the instrument gear 1032 is driven by the secondary gear 105a of the second gear assembly 105 to rotate in the first direction (e.g., direction C' illustrated in at least FIG. 4D) relative to the first central axis (e.g., axis C), then both the distal end 1031a of the instrument 1031 and the first section 1032a will be driven to rotate in the first direction (e.g., direction C' illustrated in at least FIG. 4D) relative to the first central axis (e.g., axis C).

As another example, if the first section 1032a is driven to rotate in the first direction (e.g., direction C' illustrated in at least FIG. 4D) relative to the first central axis (e.g., axis C) (e.g., by rotating the protrusion portion 1042 in a direction D', as illustrated in at least FIG. 4A, relative to the second central axis (e.g., axis D) and not rotating or "locking" the secondary gear 105a of the second gear assembly 105), then both the distal end 1031a of the instrument 1031 and the instrument gear 1032 will be driven to rotate in the first direction (e.g., direction C' illustrated in at least FIG. 4D) relative to the first central axis (e.g., axis C). In this example, it is recognized that if the secondary gear 105a of the second gear assembly 105 is "locked" or prevented from rotating and the protrusion portion 1042 is rotated in a direction D' (as illustrated in at least FIG. 4A, which may be rotated by driving the first primary gear 1041 to rotate in direction D'), the following may occur (depending on the relative position of the instrument): (1) the distal end 1031a of the instrument 1031 may be driven to rotate (e.g., direction D' illustrated in at least FIG. 4A) relative to the second central axis (e.g., axis D), and/or (2) the distal end 1031a of the instrument 1031 and the instrument gear 1032 may be driven to rotate (e.g., direction C' illustrated in at least FIG. 4D) relative to the first central axis (e.g., axis C).

As illustrated in at least FIGS. 4A-C, example embodiments of the second section 1032b may be a section or part of the intermediary instrument section 1033 that contacts with the protrusion portion 1042 (e.g., via the protrusion portion opening 1042a). The second section 1032b may be secured to the instrument gear 1032 and/or the first section 1032a, such as in example embodiments illustrated in at least FIGS. 1, 3, and 4A-C where the first section 1032a, second section 1032b, and instrument gear 1032 are on the same "arm" or segment 1033a of the intermediary instrument section 1033. Alternatively or in addition, the second section 1032b may include or be part or all of the first section 1032a. The second section 1032b may be provided in, housed in, and/or rotatable within one or more protrusion portion openings 1042a of one or more protrusion portions 1042, as described in the present disclosure.

As illustrated in at least FIGS. 1, 2A, 2B, and 4A-D, the first central axis (e.g., axis C) may be formed through the instrument gear 1032. In an example embodiment, the instrument gear 1032 may be a bevel gear, or the like, having a plurality of teeth. The instrument gear 1032 may be configurable or configured to rotate relative to the first central axis (e.g., direction C' relative to axis C, as illustrated in at least FIG. 4D). The first section 1032a and the instrument gear 1032 may be configurable or configured to be fixedly secured relative one another in such a way that, when one of either the first section 1032a or the instrument gear 1032 is driven to rotate in a first direction (e.g., in a direction C' illustrated in at least FIG. 4D) relative to the first central axis (e.g., axis C formed through the instrument gear 1032), the distal end of the instrument 1031 and the other one of the first section 1032a or the instrument gear 1032 are driven to rotate in the first direction (e.g., in a direction C' illustrated in at least FIG. 4D) relative to the first central axis (e.g., axis C).

In an example embodiment, the instrument, the instrument gear and the instrument assembly are fixedly secured relative to one another in such a way that a rotation of the instrument gear in a first direction relative to a first central axis formed through the instrument gear drives the distal end of the instrument to correspondingly rotate in the first direction relative to the first central axis. The first central axis and the instrument central axis may be orthogonal to each other at all times.

For example, when the instrument gear 1032 is driven by the secondary gear 105a of the secondary gear assembly 105 to rotate in a first direction (e.g., in a direction C' illustrated in at least FIG. 4D) relative to the first central axis (e.g., axis C), the distal end of the instrument 1031 may be driven to rotate in the first direction (e.g., in a direction C' illustrated in at least FIG. 4D) relative to the first central axis (e.g., axis C).

It is recognized in example embodiments that the intermediary instrument section 1033 of the instrument 1031 may be formed in any shape, configuration, and/or size, including a two "arm" or segment shape/configuration (e.g., "arms" or segments 1033a, 1033b illustrated in at least FIGS. 4A-B; and/or U-shaped body, C-shaped body, arch-shaped body, V-shaped body, semicircular-shaped body, etc.), a one "arm" or segment shape/configuration (e.g., "arm" or segment 1033a illustrated in FIG. 4C; and/or J-shaped body, L-shaped body, etc.), etc., so long as such shape, configuration, and size enable movements and/or positions of the instrument 1031 to be controllable by example embodiments of the first gear assembly (e.g., first gear assembly 104) and/or the second gear assembly (e.g., second gear assembly 105), as described in the present disclosure.

(ii) First Gear Assembly (e.g., First Gear Assembly 104).

In an example embodiment, the end-effector assembly 102 may include a first gear assembly (e.g., first gear assembly 104). As illustrated in at least FIGS. 2A, 2B, and 3, the first gear assembly 104 may be configurable or configured to be driven by the first motor 111 (via the first drive portion 111a and first drive shaft 111b). The first gear assembly 104 may include a first primary gear (e.g., first primary gear 1041). In an example embodiment, the first primary gear 1041 may be a bevel gear, or the like, having a plurality of teeth. The first primary gear 1041 may be configurable or configured to mesh, connect, or communicate with the first drive portion 111*a* of the first motor 111 in such a way that, when the first motor 111 drives the first drive portion 111*a* via the first drive shaft 111*b*, the first primary gear 1041 is driven to rotate relative to a second central axis D (e.g., in a direction D' illustrated in at least FIG. 4A). For example, the first primary gear 1041 and the first drive portion 111*a* of the first motor 111 may be bevel gears (and/or miter gears) having intersecting central axes (i.e., the central axis of the first drive shaft 111*b* of the first motor 111 intersects with the central axis D of the first primary gear 1041). It is to be understood in the present disclosure that the first primary gear 1041 and/or the first drive portion 111*a* of the first motor 111 may be other types of gears and/or in other types of configurations, including, but not limited to, straight gear configurations, planetary gear configurations, spiral beveled gear configurations, hypoid gear configurations, helical gear configurations, worm gear configurations, and/or any other gear and/or mechanical configurations (such as wire and pulley) without departing from the teachings of the present disclosure.

The second central axis (e.g., axis D) may be a central axis of the first primary gear 1041. The second central axis (e.g., axis D) may intersect with the first central axis (e.g., axis C), such as at a center point (e.g., point X, as illustrated in at least FIGS. 4A-D and FIG. 4E). In example embodiments, the second central axis (e.g., axis D) may intersect with the first central axis (e.g., axis C) and the instrument central axis (e.g., axis B) at the center point (e.g., point X, as illustrated in at least FIGS. 4A-E) (except for certain position(s), such as when the main straight portion 1031*c* of the elongated body of the instrument 1031 is rotated relative to the first central axis (e.g., axis C) or the center point (e.g., point X) to be parallel to and aligned with the second central axis (e.g., axis D), in which case the instrument central axis (e.g., axis B) will not be intersecting with the second central axis (e.g., axis D) at a single point of intersection (e.g., point X, as illustrated in at least FIGS. 4A-E)). In example embodiments, the second central axis (e.g., axis D) may intersect with the first central axis (e.g., axis C), and the arm segment central axis (e.g., axis A) at the center point (e.g., point X, as illustrated in at least FIGS. 4A-E) (except for certain position(s), such as when the main straight portion 1031*c* of the elongated body of the instrument 1031 is rotated relative to the second central axis (e.g., axis D) to a point where the first central axis (e.g., axis C) is parallel to and aligned with the arm segment central axis (e.g., axis A) (see, for example, FIG. 8), in which case the first central axis (e.g., axis C) will not be intersecting with the arm segment central axis (e.g., axis A) at a single point of intersection (e.g., point X, as illustrated in at least FIGS. 4A-E)). The second central axis (e.g., axis D) and the first central axis (e.g., axis C) may be configured to always be orthogonal to each other. Furthermore, the second central axis (e.g., axis D) and the arm segment central axis (e.g., axis A) may be configured to always be orthogonal to each other. Furthermore, the first central axis (e.g., axis C) and the instrument central axis (e.g., axis B) may be configured to always be orthogonal to each other.

The first gear assembly 104 may include one or more protrusion portions (e.g., protrusion portion 1042), or the like, secured to a surface of the first primary gear 1041 (e.g., the surface of the first primary gear 1041 that faces the second primary gear 1051 and/or secondary gear 105*a*). The one or more protrusion portions 1042 may be in any shape, configuration, and/or size so long as it enables the first gear assembly 104 to connect, interact, or communicate with one or more elements of the second gear assembly 105, as described in the present disclosure. For example, one or more of the protrusion portions 1042 may be configurable or configured to include a protrusion portion opening 1042*a*, or the like, for use in receiving, connecting with, and/or housing the second section 1032*b* of the instrument assembly 103, as described in the present disclosure. The one or more protrusion portions 1042 and the instrument assembly 103 may be collectively configurable or configured in such a way that the second section 1032*b* of the instrument assembly 103 is provided in, received in, held by, connected to, and/or housed in the protrusion portion opening 1042*a* and rotatable within the protrusion portion opening 1042*a*. Accordingly, each protrusion portion opening 1042*a* may be formed along the first central axis (e.g., axis C), as illustrated in at least FIGS. 2A-B.

In operation, when the instrument gear 1032 is driven to rotate (e.g., in direction C' illustrated in at least FIG. 4D) relative to the first central axis (e.g., axis C), the second section 1032*b* of the instrument assembly 103, which is provided in, received in, held by, connected to, and/or housed in the protrusion portion opening 1042*a*, correspondingly rotates within the protrusion portion opening 1042*a* so as to enable the distal end 1031*a* of the instrument 1031 to be rotated (e.g., in direction C' illustrated in at least FIG. 4D) relative to the first central axis (e.g., axis C) or the center point (e.g., point X).

In an example embodiment, when the instrument gear 1032 is driven to rotate in the first direction relative to the first central axis (e.g., axis C)., the protrusion portion opening 1042*a* and the second section of the proximal end of the instrument may be collectively configured so as to allow the second section of the proximal end of the instrument that is provided in the protrusion portion opening to rotate in the first direction relative to the first central axis.

In example embodiments where the intermediary instrument section 1033 is formed as a U-shaped body, C-shaped body, arch-shaped body, V-shaped body, semicircular-shaped body, or the like, having two "arms" or segments 1033*a*, 1033*b*, the first gear assembly 104 may include two protrusion portions 1042, or the like, as illustrated in at least FIGS. 2A-B. An end portion (e.g., the second section 1032*b*, and may also include the first section 1032*a*) of each of the "arms" or segments 1033*a*, 1033*b* of the intermediary instrument section 1033 may be provided through and received in, connected to, and/or housed in each of the protrusion portion openings 1042*a*. In this regard, the protrusion portions 1042 and the instrument assembly 103 may be configurable or configured in such a way that the two protrusion portion openings 1042*a* of the two protrusion portions 1042, the instrument gear 1032, the first section 1032*a*, and/or the second section 1032*b* are formed along the first central axis (e.g., axis C). Put differently, the first gear assembly 104 (including the first primary gear 1041, the two protrusion portions 1042, and the two protrusion portion openings 1042*a*) and the instrument assembly 103 (including the instrument gear 1032, the first section 1032*a*, the second section 1032*b*) may be formed in such a way that the first central axis (e.g., axis C) intersects the two protrusion portion openings 1042*a*, the instrument gear 1032, the first section 1032*a*, and the second section 1032*b*. It is to be understood that the first gear assembly 104 may include only one protrusion portion 1042 having one protrusion portion opening 1042*a*, or more than two protrusion portions 1042 without departing from the teachings of the present disclosure.

In operation, when the first motor 111 drives the first drive shaft 111b, which drives the first drive portion 111a to drive the first primary gear 1041 to rotate relative to the second central axis (e.g., direction D' relative to axis D, as illustrated in at least FIG. 4A), the protrusion portion 1042 is driven to rotate around the second central axis (e.g., direction D' relative to axis D, as illustrated in at least FIG. 4A) or the center point (e.g., point X). As the protrusion portion 1042 rotates around the second central axis (e.g., axis D), such a rotation effectively causes the instrument gear 1032 to be "carried" by the protrusion portion(s) 1042 to also rotate around the second central axis (e.g., in direction D' relative to axis D, as illustrated in at least FIG. 4A) or the center point (e.g., point X). When the protrusion portion 1042 is driven by the first motor via the first primary gear 1041 to rotate around the second central axis (e.g., axis D), one or more scenarios are possible, as further described below and in the present disclosure. It is to be understood that other scenarios not described in the present disclosure are also contemplated without departing from the teachings of the present disclosure.

In a first example scenario, the first motor 111 may be controlled to drive the first primary gear 1041 (as described above) and the second motor 112 may also be controlled to drive the second primary gear 1051 (via driving of the second drive shaft 112b, which drives the second drive portion 112a to drive the second primary gear 1051) to also rotate in the same direction (e.g., direction D' relative to axis D, as illustrated in at least FIG. 4A) and with the same rotational rate as that of the first primary gear 1041 relative to the second central axis (e.g., axis D). In such an example scenario, the instrument gear 1032 will not be driven to rotate relative to the first central axis (e.g., axis C). In this regard, the instrument gear 1032 can be considered to be prevented or "locked" from rotating relative to the first central axis (e.g., axis C). Furthermore, the distal end 1031a of the instrument 1031 is only caused or driven to rotate relative to the second central axis (e.g., direction D' relative to axis D, as illustrated in at least FIG. 4A) or the center point (e.g., point X).

In a second example scenario, the first motor 111 may be controlled to drive the first primary gear 1041 (as described above) and the second motor 112 may be controlled to drive the second primary gear 1051 (via driving of the second drive shaft 112b, which drives the second drive portion 112a to drive the second primary gear 1051) to rotate in a different direction (e.g., a direction opposite to direction D') and/or with a different rotational rate than that of the first primary gear 1041 relative to the second central axis (e.g., axis D) (which also includes situations where the second motor 112 is controlled to not drive the second primary gear 1051, and therefore the second primary gear 1051 does not rotate relative to the second central axis D at all). In such an example scenario, such difference in the rotational direction and/or rotational rate between that of the first primary gear 1041 and that of the second primary gear 1051 causes or drives the instrument gear 1032 to rotate relative to the first central axis (e.g., in direction C' relative to axis C, as illustrated in at least FIG. 4D). In this regard, the main straight portion 1031c of the elongated body of the instrument 1031 is caused or driven to rotate relative to both the first central axis (e.g., in direction C' relative to axis C, as illustrated in at least FIG. 4D) and the second central axis (e.g., in direction D' relative to axis D, as illustrated in at least FIG. 4A) (and driven to rotate relative to the center point X).

As described in the present disclosure, in an example embodiment, the first primary gear 1041 and the second primary gear 1051 of the second gear assembly 105 may have the same profile and parameters, for example, same diameter, same numbers/sizes of teeth, teeth depth/thickness, same gear ratio, same speed ratio and/or same face width. It is to be understood in the present disclosure that the first primary gear 1041 and/or the second primary gear 1051 of the second gear assembly 105 may be configured to have different profiles and/or parameters without departing from the teachings of the present disclosure.

(iii) Second Gear Assembly (e.g., Second Gear Assembly 105).

In an example embodiment, the end-effector assembly 102 may include a second gear assembly (e.g., second gear assembly 105). As illustrated in at least FIGS. 2A, 2B, and 3, the second gear assembly 105 may be configurable or configured to be driven by the second motor 112 (via the second drive portion 112a and second drive shaft 112b). The second gear assembly 105 may include a second primary gear (i.e., second primary gear 1051). In an example embodiment, the second gear assembly 105 may be a bevel gear, or the like, having a plurality of teeth. The second gear assembly 105 may be configurable or configured to mesh, connect, or communicate with the second drive portion 112a of the second motor 112 in such a way that, when the second motor 112 drives the second drive portion 112a via the second drive shaft 112b, the second primary gear 1051 is driven to rotate relative to a second central axis (e.g., in a direction D' illustrated in at least FIG. 4A). For example, the second primary gear 1051 and the second drive portion 112a of the second motor 112 may be bevel gears (and/or miter gears) having intersecting central axes (i.e., the central axis of the second drive shaft 112b of the first motor 112 intersecting with the central axis D of the second primary gear 1051). It is to be understood in the present disclosure that the second primary gear 1051 and/or the second drive portion 112a of the second motor 112 may be other types of gears and/or in other types of configurations, including, but not limited to, straight gear configurations, planetary gear configurations, spiral beveled gear configurations, hypoid gear configurations, helical gear configurations, worm gear configurations, and/or any other gear and/or mechanical configurations (such as wire and pulley) without departing from the teachings of the present disclosure.

In an example embodiment, the second primary gear 1051 may be configurable or configured in such a way that its central axis is aligned with the second central axis (e.g., axis D). That is, the second primary gear 1051 and first primary gear 1041 have the same central axis, namely, the second central axis (e.g., axis D).

In an example embodiment, the second primary gear 1051 may be configurable to be interlocking with the instrument gear 1032 so as to drive the instrument gear 1032 to rotate when the second primary gear 1051 rotates.

In example embodiments, the second gear assembly 105 may include a secondary gear (e.g., secondary gear 105a). The secondary gear 105a may be configurable or configured to be secured (or connected) to and coaxial with the second primary gear 1051, as illustrated in at least FIGS. 2A-B. In some embodiments, the second primary gear 1051 and the secondary gear 105a may be formed as a unitary element. The secondary gear 105a may be configurable or configured in such a way that its central axis is also aligned with the second central axis (e.g., axis D). That is, the secondary gear 105a, second primary gear 1051, and first primary gear 1041 all have the same central axis, namely, the second central axis (e.g., axis D).

As illustrated in at least FIGS. 2A, 2B, and 3, the secondary gear 105a may be configurable or configured to drive the instrument gear 1032 to rotate relative to the first central axis (e.g., axis C). In an example embodiment, the secondary gear 105a and the instrument gear 1032 may be bevel gears, or the like, having a plurality of teeth. The secondary gear 105a may be configurable or configured to mesh, connect, or communicate with the instrument gear 1032 in such a way that, when the second primary gear 1051 drives the secondary gear 105a to rotate relative to the second central axis (e.g., axis D), the secondary gear 105a drives the instrument gear 1032 to rotate relative to the first central axis (e.g., in a direction C' illustrated in at least FIG. 4D). For example, the secondary gear 105a and the instrument gear 1032 may be bevel gears (and/or miter gears) having intersecting central axes (i.e., the central axis D of the secondary gear 105a intersects with the central axis C of the instrument gear 1032). It is to be understood in the present disclosure that the secondary gear 105a and/or the instrument gear 1032 may be other types of gears and/or in other types of configurations, including, but not limited to, straight gear configurations, planetary gear configurations, spiral beveled gear configurations, hypoid gear configurations, helical gear configurations, worm gear configurations, and/or any other gear and/or mechanical configurations (such as wire and pulley) without departing from the teachings of the present disclosure.

In operation, when the second motor 112 drives the second drive shaft 112b, which drives the second drive portion 112a to drive the second primary gear 1051 to rotate relative to the second central axis (e.g., direction D' relative to axis D, as illustrated in at least FIG. 4A), the secondary gear 105a is driven by the second primary gear 1051 to rotate relative to the second central axis (e.g., direction D' relative to axis D, as illustrated in at least FIG. 4A). When the secondary gear 105a is driven by the second motor via the second primary gear 1051 to rotate around the second central axis (e.g., axis D), one or more possible scenarios are possible, as further described below and in the present disclosure.

In a first example scenario, the second motor 112 may be controlled to drive the second primary gear 1051 (as described above) and the first motor 111 may also be controlled to drive the first primary gear 1041 (via driving of the first drive shaft 111b, which drives the first drive portion 111a to drive the first primary gear 1041) to also rotate in the same direction (e.g., direction D' relative to axis D, as illustrated in at least FIG. 4A) and with the same rotational rate as that of the second primary gear 1051 relative to the second central axis (e.g., axis D). In such an example scenario, the instrument gear 1032 will not be driven to rotate relative to the first central axis (e.g., axis C). In this regard, the instrument gear 1032 can be considered to be prevented or "locked" from rotating relative to the first central axis (e.g., axis C). Furthermore, the distal end 1031a of the instrument 1031 is only driven to rotate relative to the second central axis (e.g., direction D' relative to axis D, as illustrated in at least FIG. 4A) or the center point (e.g., point X).

In a second example scenario, the second motor 112 may be controlled to drive the second primary gear 1051 (as described above) and the first motor 111 may be controlled to not drive the first primary gear 1041 (i.e., not driving the first drive shaft 111b, and therefore not driving the first drive portion 111a to drive the first primary gear 1041) to rotate relative to the second central axis (e.g., axis D). In such an example scenario, the instrument gear 1032 will be driven to rotate relative to the first central axis (e.g., axis C). In this regard, the main straight portion 1031c of the elongated body of the instrument 1031 is only caused or driven to rotate relative to the first central axis (e.g., axis C) or the center point (e.g., point X).

In a third example scenario, the second motor 112 may be controlled to drive the second primary gear 1051 (as described above) and the first motor 111 may be controlled to drive the first primary gear 1041 (via driving of the first drive shaft 111b, which drives the first drive portion 111a to drive the first primary gear 1041) to rotate in a different direction (e.g., a direction opposite to direction D') and/or with a different rotational rate than that of the second primary gear 1051 relative to the second central axis (e.g., axis D). In such an example scenario, such difference in the rotational direction and/or rotational rate between that of the first primary gear 1041 and that of the second primary gear 1051 causes or drives the instrument gear 1032 to rotate relative to the first central axis (e.g., in direction C' relative to axis C, as illustrated in at least FIG. 4D). In this regard, the main straight portion 1031c of the elongated body of the instrument 1031 is then caused or driven to rotate relative to both the first central axis (e.g., in direction C' relative to axis C, as illustrated in at least FIG. 4D) and the second central axis (e.g., in direction D' relative to axis D, as illustrated in at least FIG. 4A) (and driven to rotate relative to the center point X).

In an example embodiment, the secondary gear 105a may be configured or configurable to have a smaller diameter as compared to the second primary gear 1051. In an example embodiment, the secondary gear 105a and the instrument gear 1032 may be configured to have the same profile and parameters, for example, same diameter, same numbers/sizes of teeth, teeth depth/thickness, same gear ratio, same speed ratio and/or same face width. It is to be understood in the present disclosure that the secondary gear 105a and/or the instrument gear 1032 may be configured to have different profiles and/or parameters without departing from the teachings of the present disclosure.

It is recognized in the present disclosure that the plurality of movements of the robotic arm assembly 100, as described in the present disclosure, including the movements of the main straight portion 1031c of the elongated body of the instrument 1031 relative to the first central axis (e.g., axis C), the second central axis (e.g., axis D), instrument central axis (e.g., axis B), arm segment central axis (e.g., axis A), and/or two or more of these axes, may be provided based on example embodiments of the robotic arm assembly 100 that are configurable or configured to have a common or single point of intersection (e.g., the center point or point X, as illustrated in at least FIGS. 4A-E). For example, the robotic arm assembly 100 may be configurable or configured to have a common or single point of intersection (e.g., point X, as illustrated in at least FIGS. 4A-E) of the first central axis (e.g., axis C) and the second central axis (e.g., axis D).

As another example, the robotic arm assembly 100 may be configurable or configured to have a common or single point of intersection (e.g., point X, as illustrated in at least FIGS. 4A-E) of the first central axis (e.g., axis C), the second central axis (e.g., axis D), and the instrument central axis (e.g., axis B) (except for certain position(s), such as when the main straight portion 1031c of the elongated body of the instrument 1031 is rotated relative to the first central axis (e.g., axis C) to be parallel to and aligned with the second central axis (e.g., axis D), in which case the instrument central axis (e.g., axis B) will not be intersecting with the second central axis (e.g., axis D) at a single point of intersection (e.g., point X, as illustrated in at least FIGS. 4A-E)).

In yet another example, the robotic arm assembly 100 may be configurable or configured to have a common or single point of intersection (e.g., point X, as illustrated in at least FIGS. 4A-E) of the first central axis (e.g., axis C), the second central axis (e.g., axis D), and the arm segment central axis (e.g., axis A) (except for certain position(s), such as when the main straight portion 1031c of the elongated body of the instrument 1031 is rotated relative to the second central axis (e.g., axis D) to a point where the first central axis (e.g., axis C) is parallel to and aligned with the arm segment central axis (e.g., axis A) (see, for example, FIG. 8), in which case the first central axis (e.g., axis C) will not be intersecting with the arm segment central axis (e.g., axis A) at a single point of intersection (e.g., point X, as illustrated in at least FIGS. 4A-E)).

Movements and/or Configurations of the Robotic Arm Assembly (100, 200, 300).

Example embodiments of the robotic arm assembly 100, 200, 300 may configurable or configured to achieve a plurality of movements and/or configurations. The plurality of different movements and/or configurations of the instrument 1031 may be achieved by: controlling only the first motor 111; controlling only the second motor 112; controlling the first motor 111 and second motor 112 to rotate in the opposite direction and same rotational rates; controlling the first motor 111 and second motor 112 to rotate in opposite directions and different rotational rates; controlling the first motor 111 and second motor 112 to rotate in the same direction and same rotational rates; controlling the first motor 111 and second motor 112 to rotate in the same direction and different rotational rates; etc.

Figure 5:
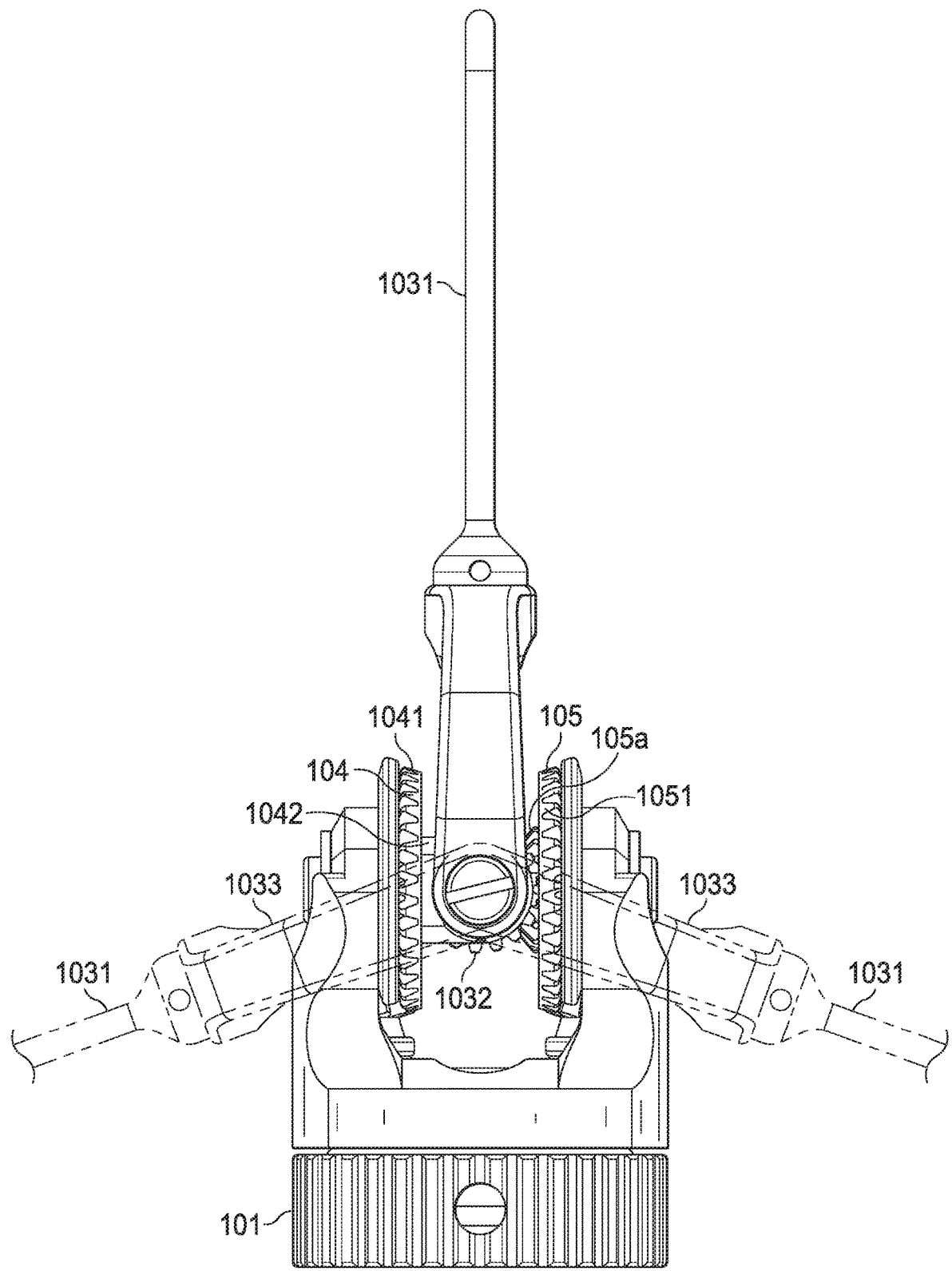
FIG. 5 is an illustration of a side view of an example embodiment of an instrument moving relative to a first central axis.
Figure 6:
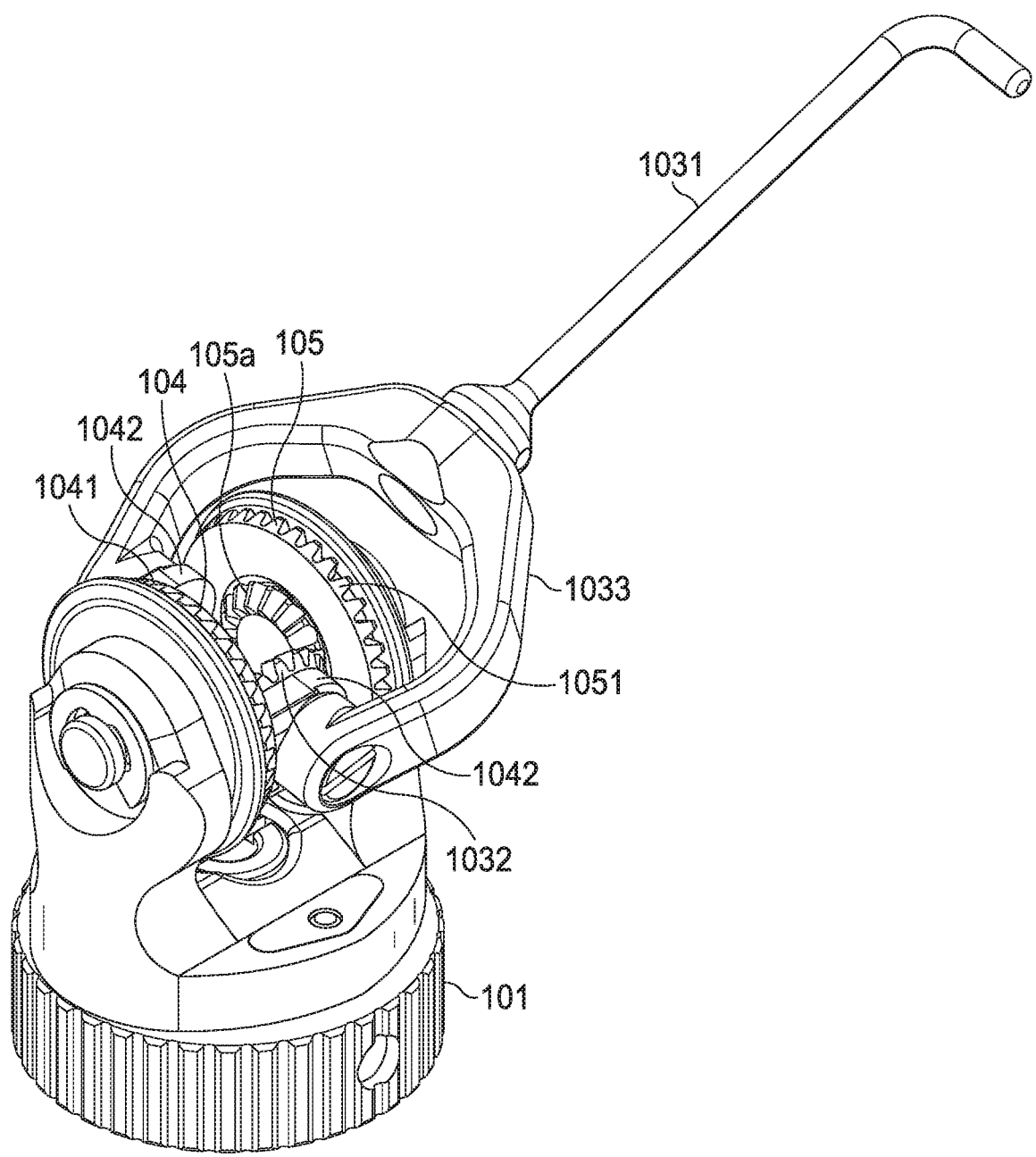
FIG. 6 is an illustration of another perspective view of an example embodiment of a robotic arm assembly.
Figure 7:
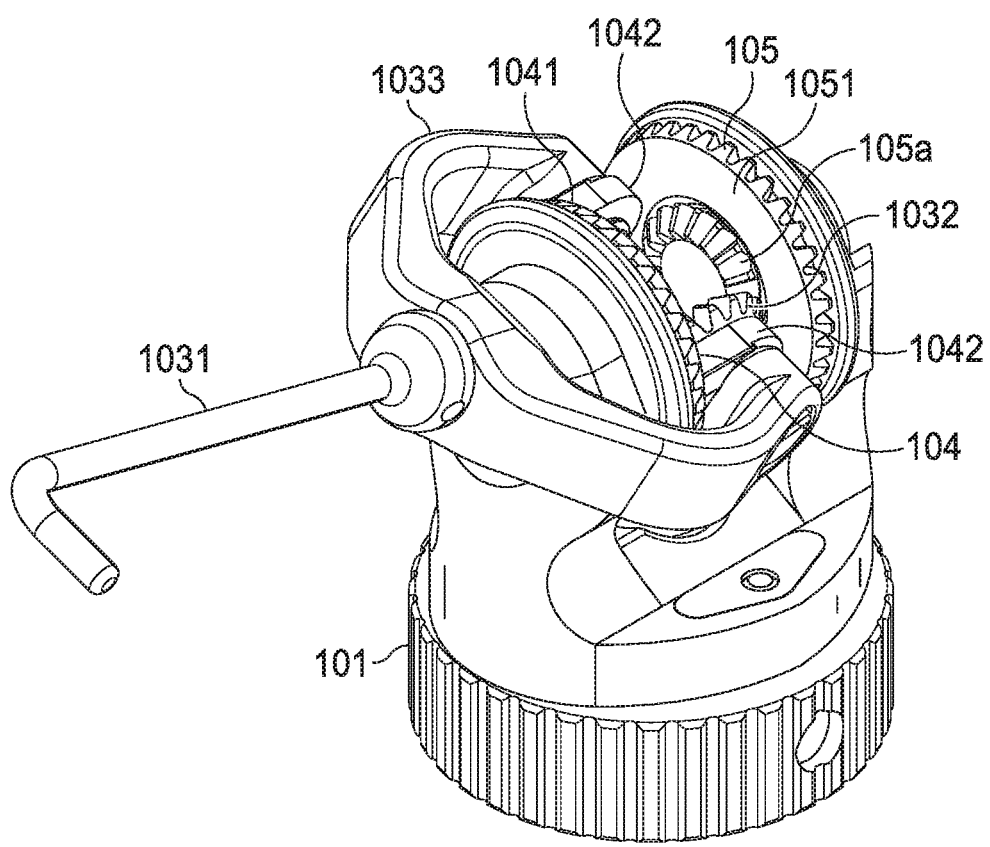
FIG. 7 is an illustration of another perspective view of an example embodiment of an instrument moving relative a second central axis.

FIG. 5, FIG. 6, and FIG. 7 illustrate example embodiments of controlling the robotic arm assembly 100, 200, 300 in such a way as to control movements and/or configurations of the instrument 1031 relative to the first central axis (e.g., axis C) or the center point (e.g., point X). For example, the first motor 111 may be controlled so as to not drive the first primary gear 1041 and the second motor 112 may be controlled so as to drive the second drive shaft 112b, which drives the second drive portion 112a to drive the second primary gear 1051 to rotate relative to the second central axis (e.g., direction D' relative to axis D, as illustrated in at least FIG. 4A). In such an example, the secondary gear 105a is driven by the second primary gear 1051 to rotate relative to the second central axis (e.g., direction D' relative to axis D, as illustrated in at least FIG. 4A). The secondary gear 105a, in turn, drives the instrument gear 1032 to rotate relative to the first central axis (e.g., axis C). In this regard, the rotation of the instrument gear 1032 causes or drives the main straight portion 1031c of the elongated body of the instrument 1031 to rotate relative to the first central axis (e.g., axis C) or the center point (e.g., point X).

Figure 8:
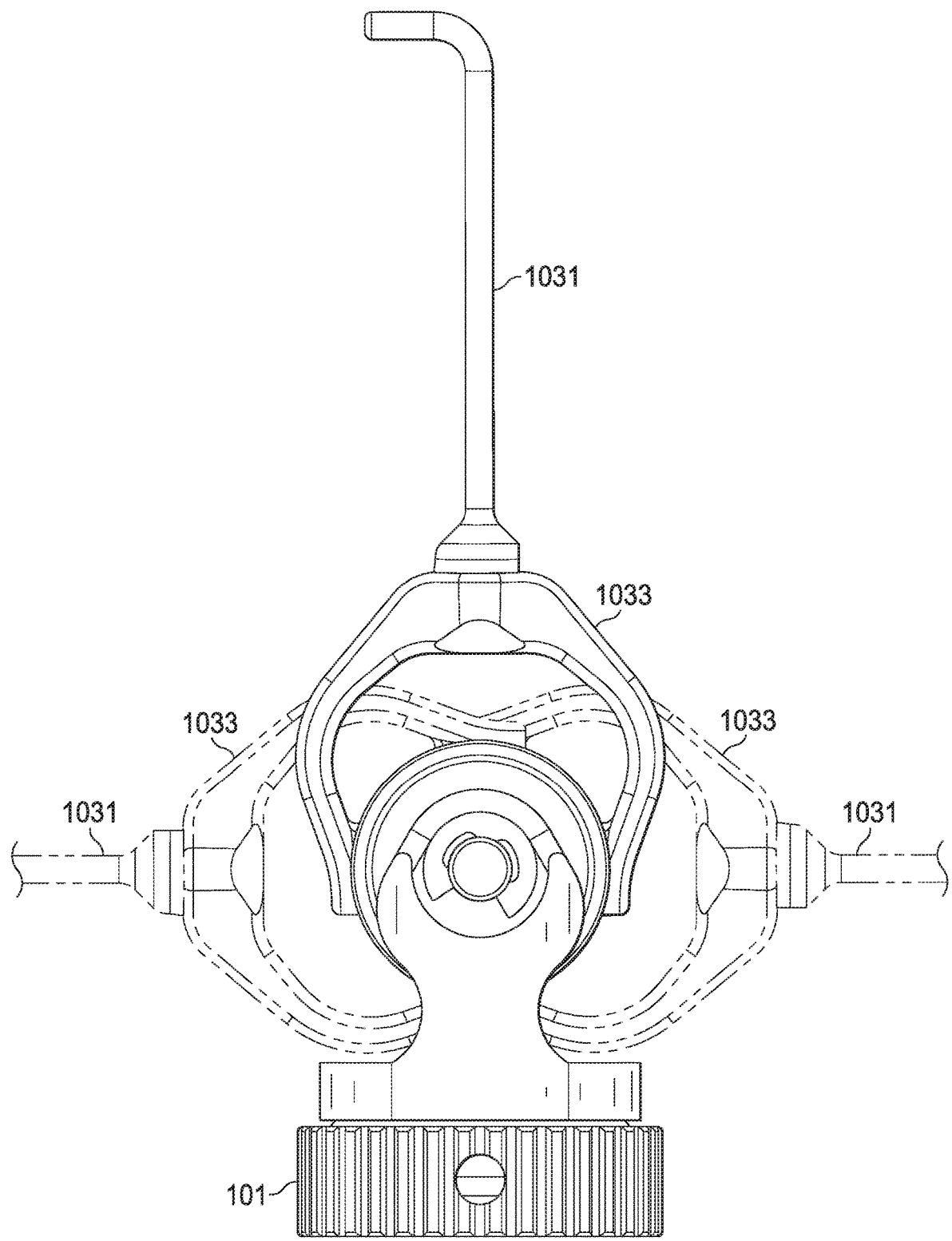
FIG. 8 is an illustration of another side view of an example embodiment of an instrument moving relative to a second central axis.
Figure 9:
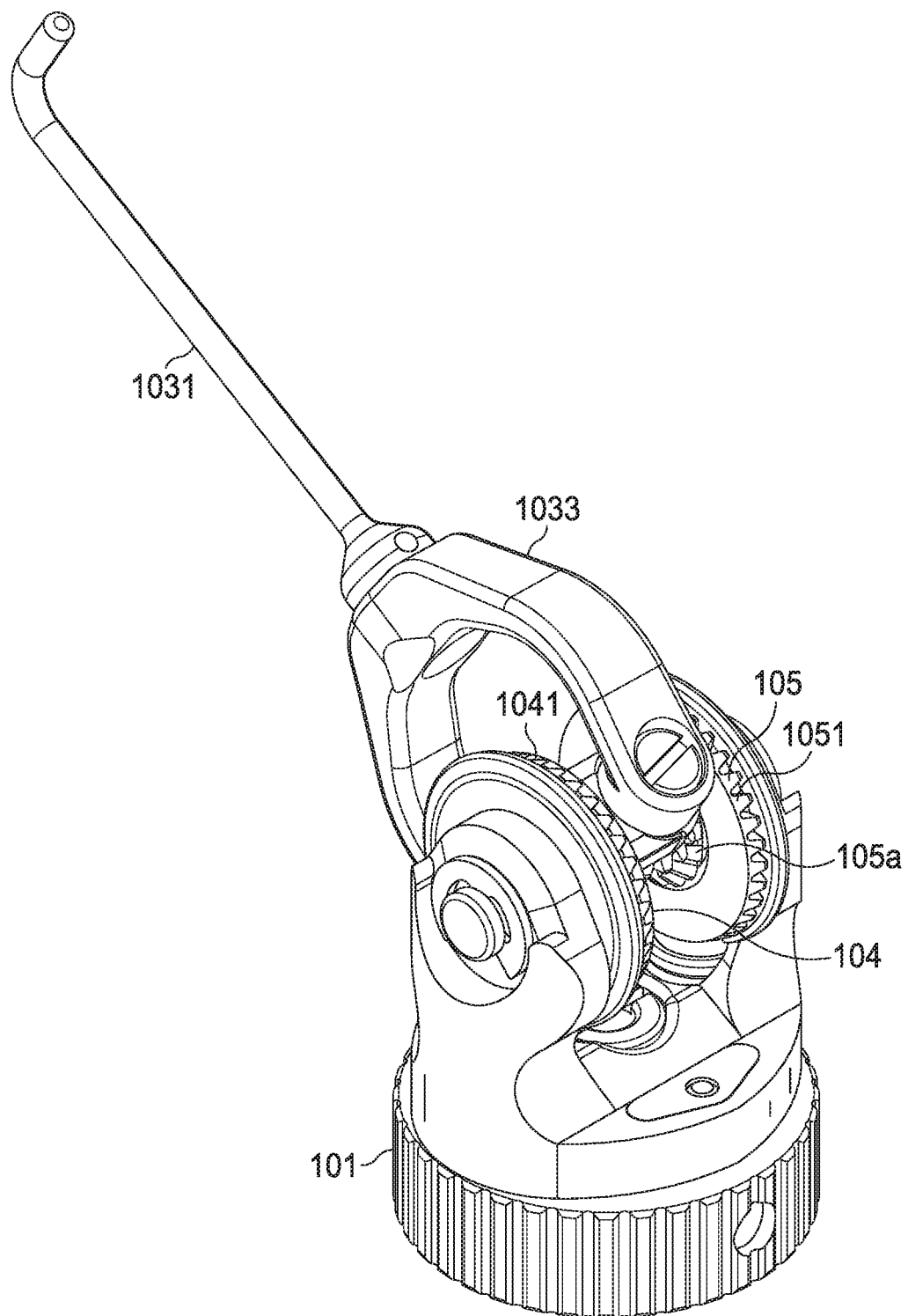
FIG. 9 is an illustration of another perspective view of an example embodiment of a robotic arm assembly.
Figure 10:
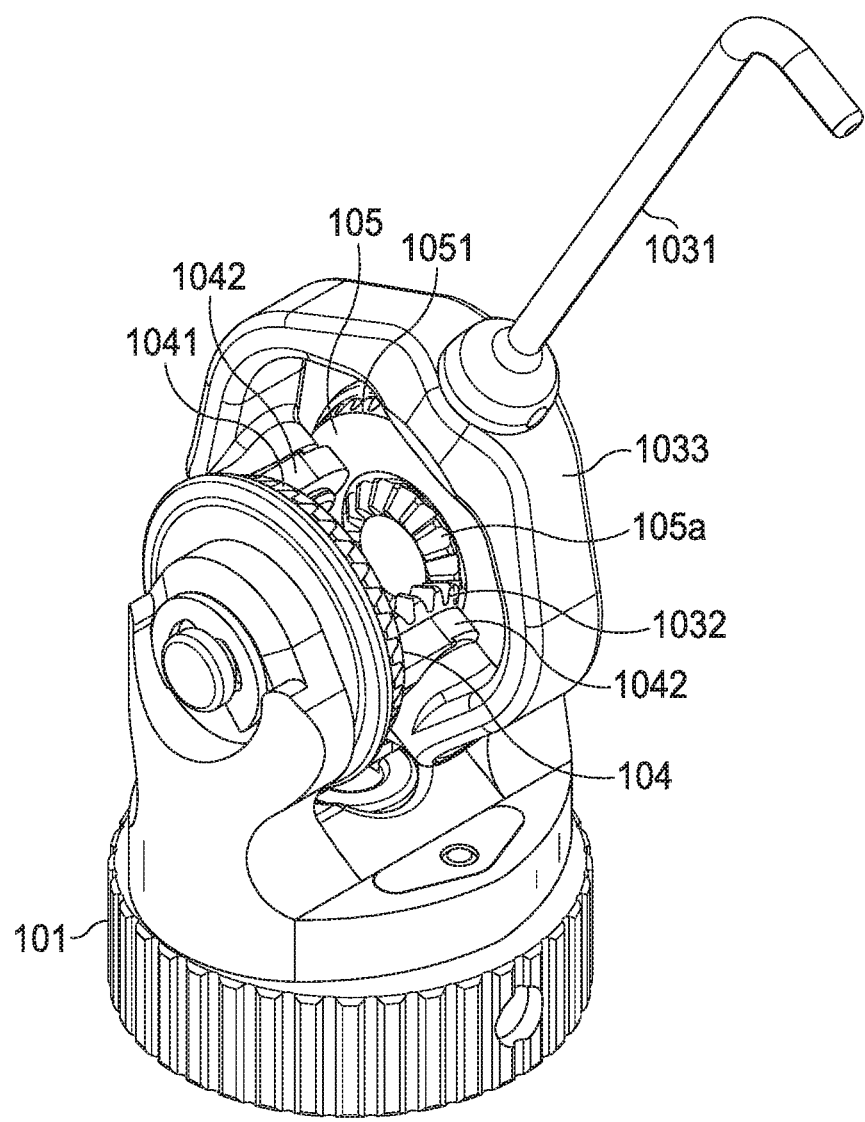
FIG. 10 is an illustration of another perspective view of an example embodiment of a robotic arm assembly.
Figure 11:
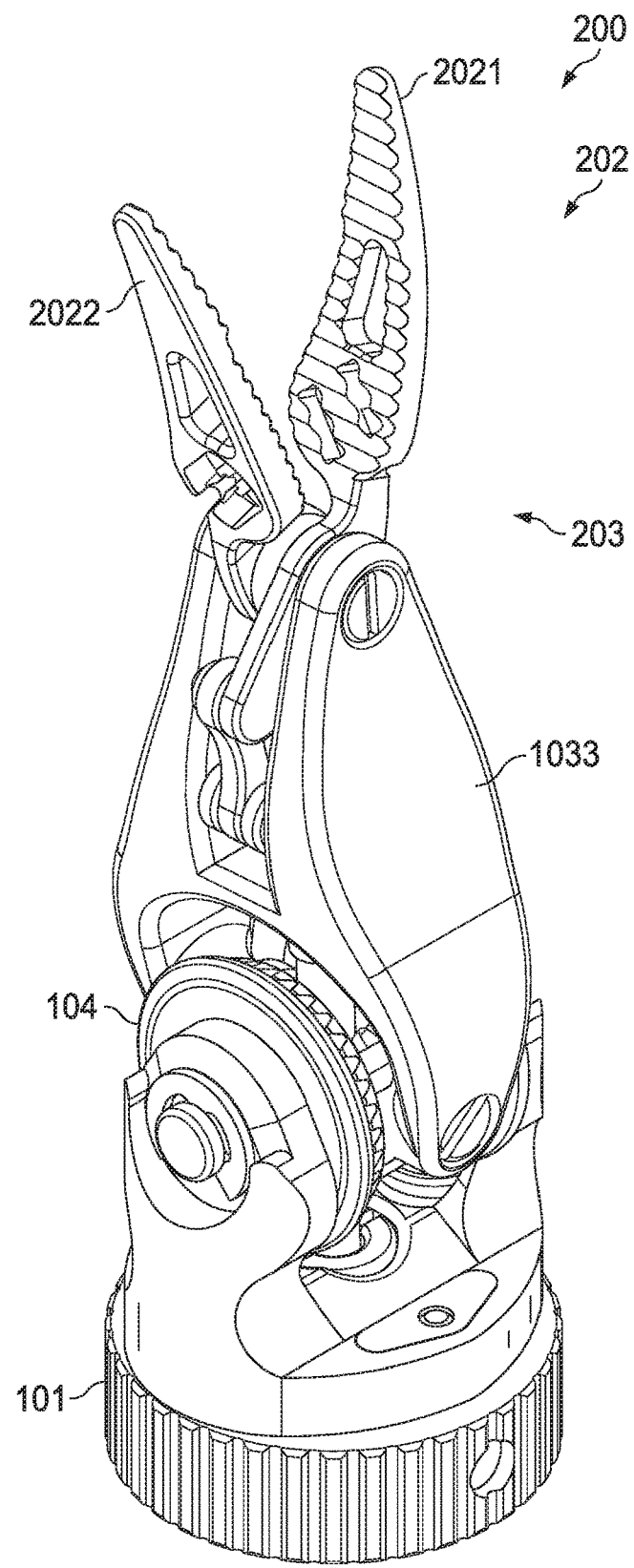
FIG. 11 is an illustration of a perspective view of an example embodiment of a robotic arm assembly configured with an instrument being a grasper.
Figure 12:
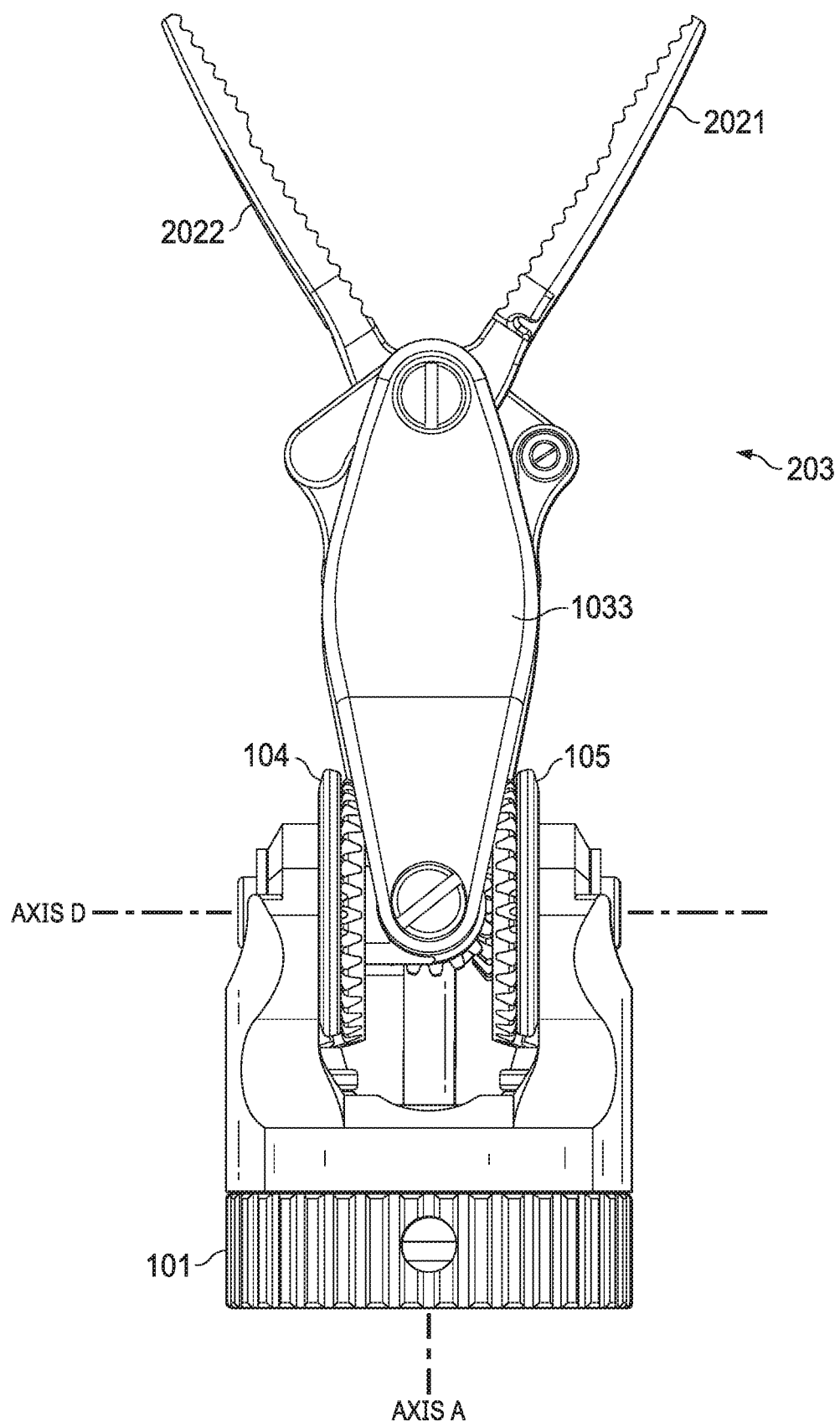
FIG. 12 is an illustration of a side view of an example embodiment of a robotic arm assembly configured with an instrument being a grasper.

FIG. 8, FIG. 9, and FIG. 10 illustrate example embodiments of controlling the robotic arm assembly 100, 200, 300 in such a way as to control movement and/or configurations of the instrument 1031 relative to the second central axis (e.g., axis D) or the center point (e.g., point X). For example, the first motor 111 and second motor 112 may be controllable or controlled so as to drive the first primary gear 1041 (via driving of the first drive shaft 111b, which drives the first drive portion 111a to drive the first primary gear 1041) and second primary gear 1051 (via driving of the second drive shaft 112b, which drives the second drive portion 112a to drive the second primary gear 1051) to rotate in the same direction (e.g., in direction D' relative to axis D, as illustrated in at least FIG. 4A) and with the same rotational rate relative to the second central axis (e.g., axis D). In such an example, the instrument gear 1032 will not be driven to rotate relative to the first central axis (e.g., axis C). In this regard, the instrument gear 1032 can be considered to be prevented or "locked" from rotating relative to the first central axis (e.g., axis C). Accordingly, the distal end 1031a of the instrument 1031 is only driven to rotate relative to the second central axis (e.g., axis D), as illustrated in at least FIGS. 8-10.

Example embodiments of the robotic arm assembly 100, 200, 300 may also be controllable or controlled in such a way that the instrument 1031 is driven to move relative to both the first central axis (e.g., axis C) and the second central axis (e.g., axis D). For example, the first motor 111 may be controllable or controlled to drive the first primary gear 1041 (via driving of the first drive shaft 111b, which drives the first drive portion 111a to drive the first primary gear 1041) to rotate relative to the second central axis (e.g., axis D) and the second motor 112 may be controlled to not drive the second primary gear 1051. In such an example, such operation of the first motor 111 and non-operation of the second motor 112 causes or drives the instrument gear 1032 to rotate relative to the first central axis (e.g., in direction C' relative to axis C, as illustrated in at least FIG. 4D). In this regard, the main straight portion 1031c of the elongated body of the instrument 1031 is caused or driven to rotate relative to both the first central axis (e.g., in direction C' relative to axis C, as illustrated in at least FIG. 4D) and the second central axis (e.g., in direction D' relative to axis D, as illustrated in at least FIG. 4A).

As another example, the first motor 111 may be controllable or controlled so as to drive the first primary gear 1041 (via driving of the first drive shaft 111b, which drives the first drive portion 111a to drive the first primary gear 1041) to rotate in a different direction (e.g., in a direction opposite to direction D') and/or with a different rotational rate than that of the second primary gear 1051 relative to the second central axis (e.g., axis D). In such an example, such difference in the rotational direction and/or rotational rate between that of the first primary gear 1041 and that of the second primary gear 1051 causes or drives the instrument gear 1032 to also rotate relative to the first central axis (e.g., in direction C' relative to axis C, as illustrated in at least FIG. 4D). In this regard, the main straight portion 1031c of the elongated body of the instrument 1031 is caused or driven to rotate relative to both the first central axis (e.g., in direction C' relative to axis C, as illustrated in at least FIG. 4D) and the second central axis (e.g., in direction D' relative to axis D, as illustrated in at least FIG. 4A).

The End-Effector Assembly (e.g., End-Effector Assembly 202, 302).

FIG. 11, FIG. 12, FIG. 13, and FIG. 14 illustrate example embodiments of the robotic arm assembly 200, 300 having end-effector assemblies with two or more instruments. Such two or more instruments may be configurable or configured to cooperate so as to function and/or operate as a single instrument, such as a grasper, cutter, Maryland grasper, etc. 202, 302.

An example embodiment of such robotic arm assemblies 200, 300 having two members 2021, 2022 cooperating to function and/or operate as a single instrument may include a third motor (e.g., third motor 313) separate from the first motor 111 and second motor 112. The third motor may include a third drive portion (e.g., third drive portion 313a)

and a third drive shaft (e.g., third drive shaft 313*b*). The third motor may be configurable or configured to cooperatively drive the first member 2021 and the second member 2022 so as to function and/or operate as a single instrument. The first and second members may be configurable or configured to move relative to the instrument central axis (e.g., axis B illustrated in at least FIG. 1).

Figure 13:
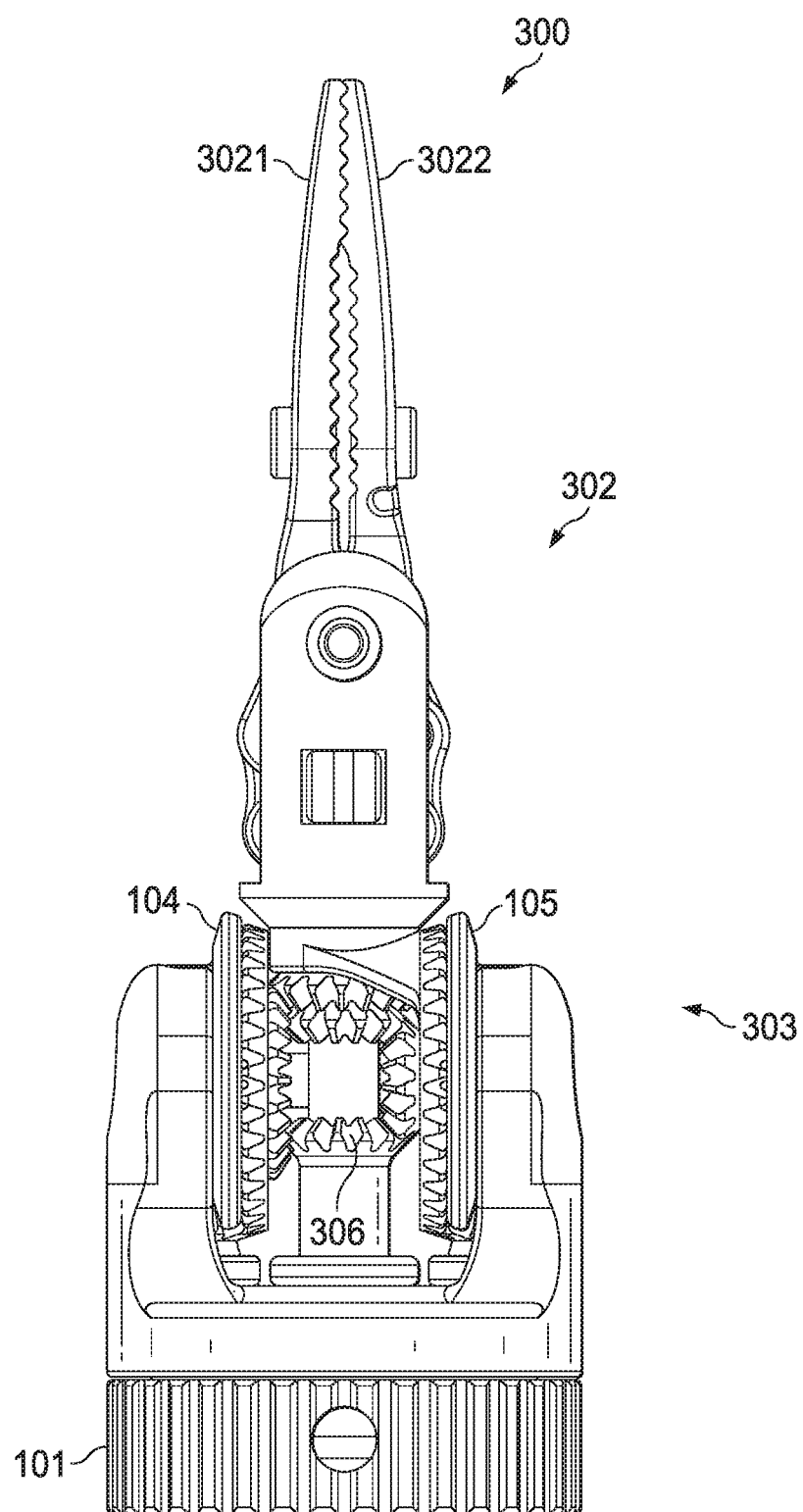
FIG. 13 is an illustration of another side view of an example embodiment of a robotic arm assembly configured with an instrument being a grasper.
Figure 14:
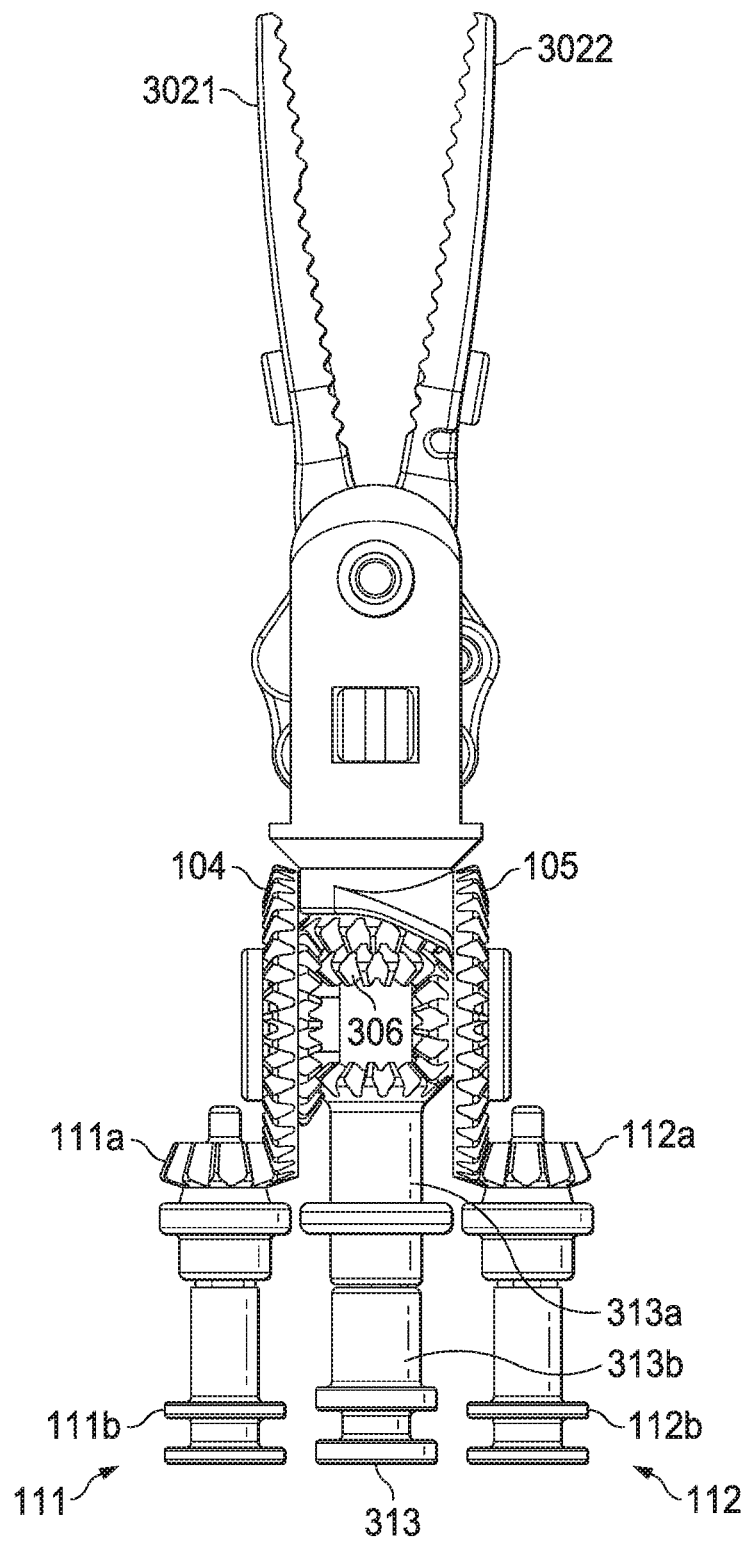
FIG. 14 is an illustration of another side view of an example embodiment of a robotic arm assembly configured with an instrument being a grasper.

In the example embodiment illustrated in at least FIGS. 13-14, robotic arm assembly 300 includes two members 3021, 3022 cooperating to function and/or operate as a single instrument. The robotic arm assembly 300 includes a third motor 313 separate from the first motor 111 and second motor 112. The third motor may include a third drive portion 313*a* and a third drive shaft 313*b*. The third motor 313 may be configurable or configured to cooperatively drive the first instrument 3021 and the second instrument 3022 so as to function and/or operate as a single instrument. The first and second instruments may be configurable or configured to move relative to the instrument central axis (e.g., axis B illustrated in at least FIG. 1). The robotic arm assembly 300 may include a third gear assembly 306 driven by the third motor. The third gear assembly 306 may be configurable or configured to drive the first member 3021 and/or second member 3022 to perform one or more actions. While various embodiments in accordance with the disclosed principles have been described above, it should be understood that they have been presented by way of example only, and are not limiting. Thus, the breadth and scope of the example embodiments described in the present disclosure should not be limited by any of the above-described exemplary embodiments, but should be defined only in accordance with the claims and their equivalents issuing from this disclosure. Furthermore, the above advantages and features are provided in described embodiments, but shall not limit the application of such issued claims to processes and structures accomplishing any or all of the above advantages.

For example, "assembly," "device," "portion," "segment," "member," "body," or other similar terms should generally be construed broadly to include one part or more than one part attached or connected together.

Various terms used herein have special meanings within the present technical field. Whether a particular term should be construed as such a "term of art" depends on the context in which that term is used. "Connected," "connecting," "attached," "attaching," "anchored," "anchoring," "in communication with," "communicating with," "associated with," "associating with," or other similar terms should generally be construed broadly to include situations where attachments, connections, and anchoring are direct between referenced elements or through one or more intermediaries between the referenced elements. These and other terms are to be construed in light of the context in which they are used in the present disclosure and as one of ordinary skill in the art would understand those terms in the disclosed context. The above definitions are not exclusive of other meanings that might be imparted to those terms based on the disclosed context.

As referred to in the present disclosure, a computing device, controller, manipulator, master input device, a processor, and/or a system may be a virtual machine, computer, node, instance, host, and/or device in a networked or non-networked computing environment. A networked computing environment may be a collection of devices connected by communication channels that facilitate communications between devices and allow devices to share resources. Also as referred to in the present disclosure, a computing device may be a device deployed to execute a program operating as a socket listener and may include software instances.

Resources may encompass any type of resource for running instances including hardware (such as servers, clients, mainframe computers, networks, network storage, data sources, memory, central processing unit time, scientific instruments, and other computing devices), as well as software, software licenses, available network services, and other non-hardware resources, or a combination thereof.

A networked computing environment may include, but is not limited to, computing grid systems, distributed computing environments, cloud computing environment, etc. Such networked computing environments include hardware and software infrastructures configured to form a virtual organization comprised of multiple resources that may be in geographically disperse locations.

Furthermore, the coverage of the present application and any patents issuing from the present application may extend to one or more communications protocols, including TCP/IP.

Words of comparison, measurement, and timing such as "at the time," "equivalent," "during," "complete," and the like should be understood to mean "substantially at the time," "substantially equivalent," "substantially during," "substantially complete," etc., where "substantially" means that such comparisons, measurements, and timings are practicable to accomplish the implicitly or expressly stated desired result.

Additionally, the section headings herein are provided for consistency with the suggestions under 37 C.F.R. 1.77 or otherwise to provide organizational cues. These headings shall not limit or characterize the invention(s) set out in any claims that may issue from this disclosure. Specifically, a description of a technology in the "Background" is not to be construed as an admission that technology is prior art to any invention(s) in this disclosure. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of such claims shall be considered on their own merits in light of this disclosure, but should not be constrained by the headings herein.

What is claimed is:

1. A robotic arm assembly, the robotic arm assembly comprising:
   an arm segment, the arm segment having an elongated body with proximal and distal ends, the elongated body of the arm segment forming an arm segment central axis; and
   an end-effector assembly securable to the distal end of the arm segment, the end-effector assembly having:
      an instrument assembly having an instrument and an instrument gear, the instrument having an elongated body with a proximal end and a distal end, the elongated body of the instrument forming an instrument central axis, the distal end of the instrument for use in performing an action, the proximal end of the instrument fixedly secured to the instrument gear in such a way that, when the instrument gear is driven to rotate in a first direction relative to a first central axis formed through the instrument gear, the distal end of the instrument is driven to rotate in the first direction relative to the first central axis; and
      a first gear assembly, the first gear assembly having:

a first primary gear, the first primary gear having a second central axis formed through the first primary gear, wherein the second central axis intersects with the first central axis, the instrument central axis, and the arm segment central axis, wherein the second central axis and the first central axis are always orthogonal to each other, and wherein the second central axis and the arm segment central axis are always orthogonal to each other; and a protrusion portion secured to the first primary gear, the protrusion portion having a protrusion portion opening, the protrusion portion and the instrument assembly collectively configured in such a way that at least a portion of the proximal end of the instrument is provided in the protrusion portion opening and rotatable within the protrusion portion opening.

2. The robotic arm assembly of claim 1, wherein the end-effector assembly further includes:
a second gear assembly, the second gear assembly having:
a second primary gear, the second primary gear positioned in such a way that its central axis is aligned with the second central axis, the second primary gear configurable to drive the instrument gear to rotate.

3. The robotic arm assembly of claim 2, wherein the second gear assembly further includes a secondary gear, the secondary gear secured to and coaxial with the second primary gear, and wherein the second primary gear drives the instrument gear via the secondary gear.

4. The robotic arm assembly of claim 3, wherein the instrument gear and the secondary gear are bevel gears, and wherein the secondary gear is configured to transmit motion to the instrument gear when the second primary gear is driven to rotate.

5. The robotic arm assembly of claim 4, wherein the secondary gear and the instrument gear are in a miter gear configuration.

6. The robotic arm assembly of claim 2, wherein the first primary gear and the second primary gear have a same diameter and same number of teeth.

7. The robotic arm assembly of claim 2, wherein the first primary gear is coaxial with the second primary gear.

8. A robotic arm assembly, the robotic arm assembly comprising:
an end-effector assembly, the end-effector assembly having:
an instrument assembly having an instrument, an instrument gear, and an instrument assembly body between the instrument and the instrument gear, the instrument having an elongated body with a proximal end and a distal end, the elongated body of the instrument forming an instrument central axis, the distal end of the instrument for use in performing an action, wherein the instrument, the instrument gear, and the instrument assembly body are fixedly secured relative to one another in such a way that a rotation of the instrument gear in a first direction relative to a first central axis formed through the instrument gear drives the distal end of the instrument to correspondingly rotate in the first direction relative to the first central axis, wherein the first central axis and the instrument central axis are always orthogonal to each other; and
a first gear assembly, the first gear assembly having:
a first primary gear, the first primary gear having a protrusion portion and a second central axis formed through the first primary gear, the protrusion portion having a protrusion portion opening fixedly positioned relative to the instrument assembly in such a way that a center axis of the protrusion portion opening is aligned with the first central axis, the protrusion portion and the instrument assembly collectively configured in such a way that a portion of the instrument assembly body is provided in the protrusion portion opening and rotatable within the protrusion portion opening, wherein the second central axis intersects with the first central axis of the instrument central axis, and wherein the second central axis and the first central axis are always orthogonal to each other.

9. The robotic arm assembly of claim 8, wherein the end-effector assembly further includes:
a second gear assembly, the second gear assembly having:
a second primary gear, the second primary gear positioned in such a way that its central axis is aligned with the second central axis, the second primary gear configured to be interlocking with the instrument gear so as to drive the instrument gear to rotate when the second primary gear rotates.

10. The robotic arm assembly of claim 9, wherein, when the second primary gear is driven to rotate in a second direction relative to the second central axis and the first primary gear is not driven to rotate, the second primary gear is configured to drive the instrument gear to rotate in the first direction relative to the first central axis.

11. The robotic arm assembly of claim 9, wherein, when the second primary gear is not driven to rotate and the first primary gear is driven to rotate in a third direction relative to the second central axis, the third direction opposite to the second direction, the first primary gear is configured to drive the instrument gear to rotate in the first direction relative to the first central axis.

12. The robotic arm assembly of claim 9, wherein, when the first and second primary gears are both driven to rotate at the same rotational rate in the same second direction relative to the second central axis, the first and second primary gears are configured to prevent the instrument gear from rotating relative to the first central axis.

13. The robotic arm assembly of claim 9, wherein, when the first primary gear is driven to rotate at a first rate in the second direction relative to the second central axis and the second primary gear is driven to rotate at a second rate in the second direction relative to the second central axis, the first rate being lesser than the second rate, the first and second primary gears are configured to drive the instrument gear to rotate in the first direction relative to the first central axis.

14. The robotic arm assembly of claim 9, wherein, when the first primary gear is driven to rotate at the second rate in the second direction relative to the second central axis and the second primary gear is driven to rotate at the first rate in the second direction relative to the second central axis, the first and second primary gears are configured to drive the instrument gear to rotate in a fourth direction relative to the first central axis, the fourth direction opposite to the first direction.

15. The robotic arm assembly of claim 9, wherein the second gear assembly further includes a secondary gear, the secondary gear secured to and coaxial with the second primary gear, and wherein the second primary gear drives the instrument gear via the secondary gear.

16. The robotic arm assembly of claim 15, wherein the instrument gear and the secondary gear are bevel gears, and wherein the secondary gear is configured to transmit motion to the instrument gear when the second primary gear is driven to rotate.

17. The robotic arm assembly of claim 15, wherein the secondary gear and the instrument gear are in a miter gear configuration.

18. The robotic arm assembly of claim 9, wherein the first primary gear and the second primary gear have a same diameter and same number of teeth.

19. The robotic arm assembly of claim 9, wherein the first primary gear is coaxial with the second primary gear.

20. A robotic arm assembly, the robotic arm assembly comprising:
   an arm segment, the arm segment having an elongated body with proximal and distal ends, the elongated body of the arm segment forming an arm segment central axis; and
   an end-effector assembly securable to the distal end of the arm segment, the end-effector assembly having:
      an instrument assembly having an instrument and an instrument gear, the instrument having an elongated body with a proximal end and a distal end, the elongated body of the instrument forming an instrument central axis, the distal end of the instrument having a first member and a second member for use in performing an action, the proximal end of the instrument fixedly secured to the instrument gear in such a way that, when the instrument gear is driven to rotate in a first direction relative to a first central axis formed through the instrument gear, the distal end of the instrument is driven to rotate in the first direction relative to the first central axis, wherein the first central axis is orthogonal to the instrument central axis; and
      a first gear assembly, the first gear assembly having:
         a first primary gear, the first primary gear having a second central axis formed through the first primary gear, wherein the second central axis intersects with the first central axis, the instrument central axis, and the arm segment central axis, wherein the second central axis and the first central axis are always orthogonal to each other, and wherein the second central axis and the arm segment central axis are always orthogonal to each other; and
         a protrusion portion secured to the first primary gear, the protrusion portion having a protrusion portion opening, the protrusion portion and the instrument assembly collectively configured in such a way that the proximal end of the instrument is provided in the protrusion portion opening and rotatable within the protrusion portion opening.

21. The robotic arm assembly of claim 20, wherein the end-effector assembly further includes:
   a second gear assembly, the second gear assembly having:
      a second primary gear, the second primary gear positioned in such a way that its central axis is aligned with the second central axis, the second primary gear configurable to drive the instrument gear to rotate.

22. The robotic arm assembly of claim 21, wherein the end-effector assembly further includes:
   a third gear assembly, the third gear assembly configurable to drive the first member and/or the second member to move relative to the instrument central axis.

23. The robotic arm assembly of claim 21, wherein, when the second primary gear is driven to rotate in a second direction relative to the second central axis and the first primary gear is not driven to rotate, the second primary gear is configured to drive the instrument gear to rotate in the first direction relative to the first central axis.

24. The robotic arm assembly of claim 21, wherein, when the second primary gear is not driven to rotate and the first primary gear is driven to rotate in a third direction relative to the second central axis, the third direction opposite to the second direction, the first primary gear is configured to drive the instrument gear to rotate in the first direction relative to the first central axis.

25. The robotic arm assembly of claim 21, wherein, when the first and second primary gears are both driven to rotate at the same rotational rate in the same second direction relative to the second central axis, the first and second primary gears are configured to prevent the instrument gear from rotating relative to the first central axis.

26. The robotic arm assembly of claim 21, wherein the second gear assembly further includes a secondary gear, the secondary gear secured to and coaxial with the second primary gear.

27. The robotic arm assembly of claim 26, wherein the instrument gear and the secondary gear are bevel gears, and wherein the secondary gear is configured to transmit motion to the instrument gear when the second primary gear is driven to rotate.

28. The robotic arm assembly of claim 26, wherein the secondary gear and the instrument gear are in a miter gear configuration.

29. The robotic arm assembly of claim 26, wherein the first primary gear and the second primary gear have a same diameter and same number of teeth.

30. The robotic arm assembly of claim 21, wherein the first primary gear is coaxial with the second primary gear.

* * * * *